United States Patent
Halley et al.

(10) Patent No.: US 7,517,902 B2
(45) Date of Patent: Apr. 14, 2009

(54) SUBSTITUTED INDAZOLES, COMPOSITIONS CONTAINING THE SAME, AND THE PREPARATION AND USE THEREOF

(75) Inventors: Frank Halley, Chaville (FR); Michel Tabart, La Norville (FR); Hervé Bouchard, Thiais (FR); Catherine Souaille, Choisy le Roi (FR); Alain Le Brun, Vigneux (FR); Fabrice Viviani, Louvres (FR); Laurence Gauzy-Lazo, Paris (FR); Pascal Desmazeau, Tigery (FR); Odile Angouillant-Boniface, Paris (FR); Bruno Filoche-Romme, Creteil (FR)

(73) Assignee: Aventis Pharma S.A., Antony (FR)

( * ) Notice: Subject to any disclaimer, the term of this patent is extended or adjusted under 35 U.S.C. 154(b) by 73 days.

(21) Appl. No.: 11/566,382

(22) Filed: Dec. 4, 2006

(65) Prior Publication Data

US 2007/0161626 A1    Jul. 12, 2007

Related U.S. Application Data

(63) Continuation of application No. PCT/FR2005/001335, filed on Jun. 1, 2005.

(30) Foreign Application Priority Data

Jun. 4, 2004   (FR) .................... 04 06042

(51) Int. Cl.
  *A61K 31/541*  (2006.01)
  *A61K 31/5377*  (2006.01)
  *C07D 417/02*  (2006.01)
  *C07D 413/02*  (2006.01)

(52) U.S. Cl. ............... 514/406; 514/227.8; 514/234.2; 514/254.06; 514/256; 544/60; 544/140; 544/333; 544/371; 546/275.7; 548/206; 548/215; 548/247; 548/312.1; 548/360.1

(58) Field of Classification Search .............. None
See application file for complete search history.

(56) References Cited

U.S. PATENT DOCUMENTS

| | | | |
|---|---|---|---|
| 6,949,579 B2 | 9/2005 | Dutruc-Rosset | |
| 7,019,011 B2 * | 3/2006 | Lesuisse et al. | .......... 514/266.2 |
| 7,119,115 B2 | 10/2006 | Tabart | |
| 2003/0199511 A1 | 10/2003 | Li et al. | |
| 2004/0092546 A1 | 5/2004 | Wei et al. | |
| 2004/0110956 A1 | 6/2004 | Lesuisse | |
| 2008/0039491 A1 | 2/2008 | Ronan | |

FOREIGN PATENT DOCUMENTS

| | | |
|---|---|---|
| EP | 1403255 | 3/2004 |
| GB | 816382 | 7/1959 |
| WO | WO 01/19828 A2 | 3/2001 |
| WO | WO03/011833 A1 | 2/2003 |
| WO | WO 03/051847 | 6/2003 |
| WO | WO03/078403 | 9/2003 |
| WO | WO 03/097610 | 11/2003 |
| WO | WO2004/022544 | 3/2004 |
| WO | WO2004/062662 | 7/2004 |
| WO | WO 2004/113304 | 12/2004 |
| WO | WO 2005/009389 A2 | 2/2005 |
| WO | WO 2005/110410 A2 | 11/2005 |
| WO | WO 2006/077319 A1 | 7/2006 |
| WO | WO 2006/099075 A2 | 9/2006 |

OTHER PUBLICATIONS

U.S. Appl. No. 12/021,638, filed Jan. 29, 2008, Bjergarde et al.

* cited by examiner

*Primary Examiner*—Kamal A Saeed
(74) *Attorney, Agent, or Firm*—Kelly L. Bender

(57) ABSTRACT

Disclosed are novel substituted indazole compounds, pharmaceutical compositions comprising such compounds, and methods of treatment comprising such compounds.

23 Claims, No Drawings

SUBSTITUTED INDAZOLES, COMPOSITIONS CONTAINING THE SAME, AND THE PREPARATION AND USE THEREOF

The present invention relates in particular to new chemical compounds, particularly to new substituted indazoles, to compositions comprising them, and to their use as medicinal products.

More particularly the invention relates to specific new indazoles displaying an anticancer activity via the modulation of the activity of proteins, and particularly of kinases.

To date, the majority of the commercial compounds used in chemotherapy pose substantial problems of side effects and of tolerance on the part of patients. These effects might be limited insofar as the medicinal products used act selectively on cancerous cells to the exclusion of the healthy cells. One of the solutions for limiting the undesirable effects of chemotherapy may therefore consist in using medicinal products which act on metabolic pathways or on constituent elements of these pathways that are expressed primarily in cancerous cells and which would be expressed little or not at all in healthy cells.

Protein kinases are a class of enzymes which catalyze the phosphorylation of hydroxyl groups of specific protein residues such as tyrosine, serine or threonine residues. Such phosphorylations can widely modify the function of proteins; for instance, protein kinases play an important part in regulating a wide variety of cell processes, including, in particular, metabolism, cell proliferation, cell differentiation, cell migration or cell survival. Among the various cell functions in which the activity of a protein kinase is involved, certain processes represent attractive targets for treating cancerous diseases and also other diseases.

Accordingly one of the objects of the present invention is to provide compositions having an anticancer activity, acting in particular with respect to kinases. Among the kinases for which modulation of the activity is desired, Aurora2, CDK4, KDR and Tie2 are preferred.

The representation of indazoles among marketed pharmaceutical products is relatively low.

The following documents propose the therapeutic use of indazoles substituted in position 3 by an amide and in position 6 by a substituted aryl:

Patent application WO 03/078403 discloses indazoles which are substituted in position 3 by amides and are useful for treating numerous pathologies, particularly pathologies associated with the central nervous system. An oncological use, although claimed, is not demonstrated.

Patent application WO 03/051847 discloses indazoles which are substituted in position 3 by amides and are useful for treating numerous pathologies, particularly pathologies associated with the central nervous system. An oncological use, although claimed, is not demonstrated.

Surprisingly it has now been found that indazoles substituted in position 3 by a substituent NH-M-R3, where M and R3 are as defined below, and in position 6 by a substituted heteroaromatic or aromatic substituent exhibit a substantial inhibitory activity on kinases, and particularly against KDR and Tie2.

One of the merits of the invention is to have found that the substitution of indazole in position 6 by an appropriate moiety brings about substantial inhibition of the kinases KDR and Tie2. Another of the merits of the invention is to have found the substitution of indazole in position 3 by a substituent NH-M-R3 where M and R3 are as defined below, is a determinant factor in obtaining satisfactory activity on the two kinases. Accordingly, a change of functional group in position 3 of the indazole brings about, systematically, a drop in the KDR- and Tie2-inhibitory activity.

Moreover, another of the merits of the invention is to have demonstrated that, even when the indazole is correctly substituted by an appropriate moiety, it is indispensable for the nitrogen in position 1 of the indazole not to be substituted, in order to preserve a satisfactory inhibitory activity.

These products correspond to formula (I) below:

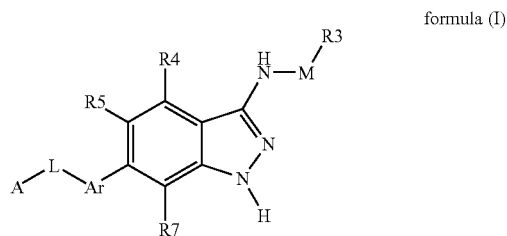

formula (I)

in which:

1) A is selected from the group consisting of: H, aryl, heteroaryl, substituted aryl, substituted heteroaryl;

2) Ar is selected from the group consisting of: aryl, heteroaryl, substituted aryl, substituted heteroaryl;

3) L is selected from the group consisting of: bond, CO, NH, CO—NH, NH—CO, NH—SO, NH—SO$_2$, NH—CO—NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH, CH$_2$—NH—CO—NH, NH—CO—NH—CH$_2$;

4) M is selected from the group consisting of: bond, CO, NH, CO—NH, CS—NH, NH—CO, NH—SO, NH—SO$_2$, CO—NH—SO$_2$, NH—CH$_2$, CH$_2$—CO—NH, NH—CO—CH$_2$, NH—CH$_2$—CO, CO—CH$_2$—NH;

5) R3 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, substituted alkynyl;

6) R4, R5 and R7 are independently selected from the group consisting of: H, halogen, R2, CN, O(R2), OC(O)(R2), OC(O)N(R2)(R1), OS(O$_2$)(R2), N(R2)(R1), N=C(R2)(R1), N(R2)C(O)(R1), N(R2)C(O)O(R1), N(R6)C(O)N(R2)(R1), N(R6)C(S)N(R2)(R1), N(R2)S(O$_2$)(R1), C(O)(R2), C(O)O(R2), C(O)N(R2)(R1), C(=N(R1))(R2), C(=N(OR1))(R2), S(R2), S(O)(R2), S(O$_2$)(R2), S(O$_2$)O(R2), S(O$_2$)N(R2)(R1); in which each R2, R1, R6 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, substituted alkynyl; in which, when R2 and R1 are simultaneously present on one of R4, R5 and R7, they may be linked to one another to form a ring.

In the products of formula (I), Ar-L-A is advantageously:

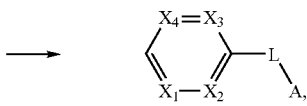

in which each X1, X2, X3 and X4 is independently selected from N and C—R11, in which R11 is selected from the group consisting of: H, halogen, R2, CN, O(R2), OC(O)(R2), OC(O)N(R2)(R1), OS(O$_2$)(R2), N(R2)(R1), N=C(R2)(R1), N(R2)C(O)(R1), N(R2)C(O)O(R1), N(R6)C(O)N(R2)(R1), N(R6)C(S)N(R2)(R1), N(R2)S(O$_2$)(R1), C(O)(R2), C(O)O (R2), C(O)N(R2)(R1), C(=N(R1))(R2), C(=N(OR1))(R2), S(R2), S(O)(R2), S(O$_2$)(R2), S(O$_2$)O(R2), S(O$_2$)N(R2)(R1); in which each R2, R1, R6 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, substituted alkynyl; in which, when R2 and R1 are simultaneously present on R11, they may be linked to one another to form a ring.

Substituents R11 selected from the group consisting of H, F, Cl, methyl, NH$_2$, OCF$_3$, and CONH$_2$ are preferred.

R4, R5 and R7 are advantageously selected from H, F, Cl, Br and methyl.

R7 is preferably selected from the group consisting of F, Cl, Br and methyl, in which F is more particularly preferred. This is because it has been found that the substitution of R7 by a fluorine atom provides a significant improvement in the biochemical activity, especially as regards the inhibitory activity on kinase, and in particular on Tie2 and KDR.

L-A is advantageously selected from NH$_2$, NH-A, NH—CO—NH-A and NH—SO$_2$-A.

A preferred substituent A is advantageously selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl, and benzothiazolyl, it being possible for each of the preceding substituents to be optionally substituted.

A more preferred substituent A is selected from phenyl, isoxazolyl, substituted phenyl, and substituted isoxazolyl.

A is preferably substituted by a first substituent selected from the group consisting of alkyl, halogenated alkyl, alkylene, alkynyl, aryl, O-alkyl, O-aryl, O-heteroaryl, S-alkyl, S-aryl, S-heteroaryl, each being optionally substituted by a substituent selected from (C1-C3)alkyl, halogen, O—(C1-C3)alkyl.

A is preferably substituted by a second substituent selected from the group consisting of F, Cl, Br, I, OH, SH, SO$_3$M, COOM, CN, NO$_2$, CON(R8)(R9), N(R8)(R9)CO(R8), (C1-C3)alkyl-OH, (C1-C3)alkyl-N(R8)(R9), (C1-C3)alkyl-(R10), (C1-C3)alkyl-COOH, N(R8)(R9); in which R8 and R9 are independently selected from H, (C1-C3)alkyl, (C1-C3)alkylOH, (C1-C3)alkylNH$_2$, (C1-C3)alkylCOOM, (C1-C3)alkylSO$_3$M; in which, when R8 and R9 are simultaneously other than H, they may be linked to form a ring; in which M is H or an alkali metal cation selected from Li, Na and K; and in which R10 is H or a nonaromatic heterocycle optionally substituted by comprising 2 to 7 carbon atoms, and 1 to 3 heteroatoms selected from N, O and S.

A substituent A which is particularly effective for obtaining an inhibition of kinase activity is selected from phenyl and isoxazolyl, each being substituted by at least one substituent selected from halogen, (C1-C4)alkyl, halogenated (C1-C3) alkyl, O—(C1-C4)alkyl, S—(C1-C4)alkyl, halogenated O—(C1-C4)alkyl, and halogenated S—(C1-C4)alkyl.

Moreover, a preferred substituent M will advantageously be selected from the group consisting of bond, CO, CO—NH, and SO$_2$.

R3 is preferably selected from the group consisting of aryl, heteroaryl, substituted aryl, and substituted heteroaryl. A more particularly preferred R3 is substituted heteroaryl. Among substituted heteroaryls, thienyl, pyrrolyl, furyl, indolyl, oxazolyl, isoxazolyl, thiazolyl, isothiazolyl, imidazolyl, indazolyl, pyridyl, pyrimidyl, pyrazolyl, and pyridazinyl are heteroaryls of choice.

R4 and R5 are advantageously H. This is because, in this case, a significant improvement has been observed in the activity with respect to kinases KDR and/or Tie2, and generally an improvement in the solubility.

Acceptable products corresponding to the required inhibitory activity conditions may selected from the group consisting of:

1-[4-(3-amino-1H-indazol-6-yl)phenyl]-3-(2-fluoro-5-trifluoromethylphenyl)urea

N-{6-[4-(2,3-dichlorobenzenesulfonylamino)phenyl]-1H-indazol-3-yl}(thiophen-3-yl-carboxamide)

N-[4-(3-amino-1H-indazol-6-yl)phenyl]-2,3-dichlorobenzenesulfonamide.

Other acceptable products, in which R7 is preferably a halogen, more preferably fluorine, corresponding to the required inhibitory activity conditions and displaying in fact a greater activity than analogs in which R7 is other than a halogen, may be selected from the group consisting of:

1-[4-(3-amino-7-fluoro-1H-indazol-6-yl)phenyl]-3-(2-fluoro-5-trifluoromethylphenyl)urea 1-(2-fluoro-5-trifluoromethylphenyl)-3-{4-[7-fluoro-3-(thiophen-3-yl-carbonylamino)-1H-indazol-6-yl] phenyl}urea N-{6-[4-(2,3-dichlorobenzenesulfonylamino)phenyl]-7-fluoro-1H-indazol-3-yl}(thiophen-3-yl-carboxamide)

N-[4-(3-amino-7-fluoro-1H-indazol-6-yl)phenyl]-2,3-dichlorobenzenesulfonamide 1-(2-fluoro-5-trifluoromethylphenyl)-3-{4-[4,5,7-trifluoro-3-(thiophen-3-ylcarbonylamino)-1H-indazol-6-yl] phenyl}urea N-[6-(4-aminophenyl)-7-fluoro-1H-indazol-3-yl](thiophen-3-ylcarboxamide).

A product in accordance with the invention may exist in a:
1) Nonchiral, or
2) Racemic, or
3) stereoisomerically enriched, or
4) enantiomerically enriched form;

and can be optionally converted to salt form.

A product in accordance with the invention can be used for preparing a medicinal product which is useful for treating a pathological condition, in particular a cancer.

The present invention also relates to therapeutic compositions comprising a product according to the invention, in combination with an excipient which is acceptable pharmaceutically in accordance with the selected mode of administration. The pharmaceutical composition may be present in solid or liquid form or in the form of liposomes.

Among solid compositions mention may be made of powders, gelatin capsules and tablets. Among oral forms it is also possible to include solid forms protected against the acidic environment of the stomach. The carriers used for solid forms are composed in particular of inorganic carriers such as phosphates and carbonates or of organic carriers such as lactose, celluloses, starch or polymers. The liquid forms are composed of solutions, suspensions or dispersions. As dispersive carrier they comprise alternatively water, an organic solvent (ethanol, NMP or others) or mixtures of surfactants and solvents or of complexing agents and solvents.

The liquid forms will be preferably injectable and, consequently, will have a formulation which is acceptable for such a use.

Acceptable routes of administration by injection include intravenous, intraperitoneal, intramuscular and subcutaneous routes, the intravenous route being commonly preferred.

The dose that is administered of the compounds of the invention will be adjusted by the practitioner as a function of the route of administration to the patient and of the patient's condition.

The compounds of the present invention can be administered alone or as a mixture with other anticancer agents. The possible combinations include the following:

alkylating agents and especially cyclophosphamide, melphalan, ifosfamide, chlorambucil, busulfan, thiotepa, prednimustine, carmustine, lomustine, semustine, steptozotocin, decarbazine, temozolomide, procarbazine and hexamethylmelamine platinum derivatives such as, in particular, cisplatin, carboplatin or oxaliplatin antibiotics such as, in particular, bleomycin, mitomycin and dactinomycin antimicrotubule agents such as, in particular, vinblastine, vincristine, vindesine, vinorelbine or taxoids (paclitaxel and docetaxel)

anthracyclines such as, in particular, doxorubicin, daunorubicin, idarijbicin, epirubicin, mitoxantron and losoxantron topoisomerase group I and group II inhibitors, such as etoposide, teniposide, amsacrine, irinotecan, topotecan and tomudex fluoropyrimidinies such as 5-fluorouracil, UFT and floxuridine cytidine analogs, such as 5-azacytidine, cytarabine, gemcitabine, 6-mercaptomurine and 6-thioguanine adenosine analogs such as pentostatin, cytarabine or fludarabine phosphate methotrexate and folinic acid various enzymes and compounds, such as L-asparaginase, hydroxyurea, trans-retinoic acid, suramin, dexrazoxane, amifostine, herceptine and also estrogenic and androgenic hormones antivascular agents such as derivatives of combretastatin or of coichicine and their prodrugs.

It is also possible to combine the compounds of the present invention with a radiation treatment. These treatments may be administered simultaneously, separately or sequentially. The treatment will be adjusted by the practitioner as a function of the patient to be treated.

The products of the invention are useful as agents for inhibiting a reaction which is catalyzed by a kinase. KDR and Tie2 are kinases for which the products of the invention will be particularly useful as inhibitors.

The reasons for which these kinases are selected are given below:

KDR

KDR (Kinase insert Domain Receptor), also known as VEGF-R2 (Vascular Endothelial Growth Factor Receptor 2), is expressed only in endothelial cells. This receptor binds to the angiogenic growth factor VEGF and thus acts as a mediator to a transduction signal via the activation of its intracellular kinase domain. Direct inhibition of the kinase activity of VEGF-R2 makes it possible to reduce the phenomenon of angiogenesis in the presence of exogenous VEGF (Vascular Endothelial Growth Factor) (Strawn et al., *Cancer Research,* 1996, vol. 56, p. 3540-3545). This process has been demonstrated in particular using VEGF-R2 mutants (Millauer et al., *Cancer Research,* 1996, vol. 56, p. 1615-1620). The VEGF-R2 receptor does not appear to have any function in adults other than that related to the angiogenic activity of VEGF. Consequently, a selective inhibitor of the kinase activity of VEGF-R2 should show only slight toxicity.

In addition to this central role in the angiogenic dynamic process, recent results suggest that the expression of VEGF contributes to the survival of tumor cells after chemotherapy and radiotherapy, underlining the potential synergy of KDR inhibitors with other agents (Lee et al. *Cancer Research,* 2000, vol. 60, p. 5565-5570).

Tie2

Tie-2 (TEK) is a member of a class of tyrosine kinase receptors, specific for endothelial cells. Tie2 is the first receptor possessing tyrosine kinase activity for which both the agonist (angiopoietin 1 or Ang1) which stimulates autophosphorylation of the receptor and cell signaling [S. Davis et al (1996) *Cell* 87, 1161-1169] and the antagonist (angiopoietin 2 or Ang2) [P. C. Maisonpierre et al. (1997) *Science* 277, 55-60] are known. Angiopoietin 1 can act synergistically with VEGF in the final stages of neoangiogenesis [Asahara T. *Circ. Res.* (1998) 233-240]. Knockout experiments and transgenic manipulations of the expression of Tie2 or of Ang1 result in animals which exhibit vascularization defects [D. J. Dumont et al (1994) *Genes Dev.* 8, 1897-1909 and C. Suri (1996) *Cell* 87, 1171-1180]. The binding of Ang1 to its receptor results in the autophosphorylation of the kinase domain of Tie2 which is essential for neovascularization and also for the recruitment and interaction of the vessels with pericytes and smooth muscle cells; these phenomena contribute to the maturation and stability of the newly formed vessels [P. C. Maisonpierre et al (1997) *Science* 277, 55-60]. Lin et al (1997) *J. Clin. Invest.* 100, 8: 2072-2078 and P. Lin (1998) *PNAS* 95, 8829-8834], have shown an inhibition of tumor growth and vascularization and also a decrease in lung metastases during adenoviral infections or during injections of the extracellular domain of Tie-2 (Tek) in breast tumor and melanoma xenograph models.

Tie2 inhibitors can be used in situations where neovascularization takes place inappropriately (i.e., in diabetic retinopathy, chronic inflammation, psoriasis, Kaposi's sarcoma, chronic neovascularization due to macular degeneration, rheumatoid arthritis, infantile hemoangioma and cancers).

CDK

The progression of the cell cycle is often controlled by cyclin-dependent kinases (CDKS) which are activated by interaction with proteins belonging to the cyclin class, an activation which ends with the phosphorylation of substrates and, ultimately, with cell division. In addition, the endogenous CDK inhibitors which are activated (INK4 and KIP/CIP class) negatively regulate CDK activity. The growth of normal cells is due to a balance between CDK activators (cyclins) and endogenous CDK inhibitors. In a number of types of cancers, the aberrant activity or expression of a number of these cell-cycle regulators has been described.

Cyclin E activates the Cdk2 kinase, which subsequently acts to phosphorylate the protein pRb (retinoblastoma protein), resulting in irreversible engagement in cell division and in a transition to the S phase (P L Toogood, Medicinal Research Reviews (2001), 21(6); 487-498). Kinase CDK2 and possibly CDK3 are necessary for progression in the G1 phase and entry into S phase. During the formation of a complex with cyclin E, they maintain the hyperphosphorylation of pRb so as to aid the progression of the G1 phase to S phase. In complexes with cyclin A, CDK2 plays a part in the inactivation of E2F and is necessary for the realization of the S phase (T D. Davies et al. (2001) Structure 9, 389-3).

The CDK1/cyclin B complex regulates the progression of the cell cycle between the G2 phase and the M phase. Negative regulation of the CDK/cyclin B complex prevents normal cells from entering into S phase before the G2 phase has been properly and completely realized (K. K. Roy and E. A. Sausville Current Pharmaceutical Design, 2001, 7, 1669-1687).

A level of regulation of CDK activity exists. Cyclin-dependent kinase activators (CAKs) have a positive regulatory action on CDKS. CAK phosphorylates the CDKs on the threonine residue so as to render the target enzyme completely active.

The presence of defects in molecules involved in the cell cycle brings about the activation of the CDKs and the progression of the cycle; it is normal to wish to inhibit the activity of CDK enzymes in order to block cell growth in cancerous cells.

Aurora

Many proteins involved in chromosome segregation and spindle assembly have been identified in yeast and drosophilia. Disruption of these proteins leads to non-segregation of chromosomes and to monopolar or disorganized spindles. Among these proteins, certain kinases, including Aurora and Ipl1, originating respectively from drosophilia and from *S. cerevisiae*, are necessary for chromosome segregation and centrosome separation. A human analog of yeast Ipl1 has recently been cloned and characterized by various laboratories. This kinase, called aurora2, STK15 or BTAK, belongs to the serine/threonine kinase class. Bischoff et al. have shown that Aurora2 is oncogenic and is amplified in human colorectal cancers (EMBO J, 1998, 17, 3052-3065). This has also been exemplified in cancers involving epithelial tumors such as breast cancer.

Definitions

The term "halogen" refers to an element selected from F, Cl, Br, and I.

The term "alkyl" refers to a saturated, linear or branched, hydrocarbon substituent having from 1 to 12 carbon atoms. The substituents methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl, and dodecyl are examples of an alkyl substituent.

The term "alkylene" refers to a linear or branched hydrocarbon substituent having one or more unsaturations and from 2 to 12 carbon atoms. The substituents ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, buta-1,3-dienyl, 1-methylidenylprop-2-enyl, Z-2-methylbuta-1,3-dienyl, E-2-methylbuta-1,3-dienyl, 2-methyl-1-methylidenylprop-2-enyl, undec-1-enyl and undec-10-enyl are examples of an alkylene substituent.

The term "alkynyl" refers to a linear or branched hydrocarbon substituent having at least two unsaturations carried by a pair of vicinal carbon atoms, and having from 2 to 12 carbon atoms. The substituents ethynyl; prop-1-ynyl; prop-2-ynyl; and but-1-ynyl are examples of an alkynyl substituent.

The term "aryl" refers to a mono- or polycyclic aromatic substituent having from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of an aryl substituent.

The term "heteroaryl" refers to a mono- or polycyclic heteroaromatic substituent having from 1 to 13 carbon atoms and from 1 to 4 heteroatoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl and acridyl are examples of a heteroaryl substituent.

The term "heteroatom" here refers to an at least divalent atom other than carbon. N; O; S; and Se are examples of a heteroatom.

The term "cycloalkyl" refers to a saturated or partially unsaturated cyclic hydrocarbon substituent having from 3 to 12 carbon atoms. The substituents cyclopropyl, cyclobutyl, cyclopentyl, cyclopentenyl, cyclopentadienyl, cyclohexyl, cyclohexenyl, cycloheptyl, bicyclo[2.2.1]heptyl, cyclooctyl, bicyclo[2.2.2]octyl, adamantyl and perhydronaphthyl are examples of a cycloalkyl substituent.

The term "heterocyclyl" refers to a saturated or partially unsaturated cyclic hydrocarbon substituent having from 1 to 13 carbon atoms and from 1 to 4 heteroatoms. Preferably the saturated or partially unsaturated cyclic hydrocarbon substituent will be monocyclic and will comprise 4 or 5 carbon atoms and 1 to 3 heteroatoms.

The term "substituted" refers to a substituent other than H, for example halogen, alkyl, aryl, heteroaryl, cycloalkyl, heterocyclyl, alkylene, alkynyl, OH, O-alkyl, O-alkylene, O-aryl, O-heteroaryl, $NH_2$, NH-alkyl, NH-aryl, NH-heteroaryl, SH, S-alkyl, S-aryl, $S(O_2)H$, $S(O_2)$-alkyl, $S(O_2)$-aryl, $SO_3H$, $SO_3$-alkyl, $SO_3$-aryl, CHO, C(O)-alkyl, C(O)-aryl, C(O)OH, C(O)O-alkyl, C(O)O-aryl; OC(O)-alkyl, OC(O)-aryl, $C(O)NH_2$; C(O)NH-alkyl, C(O)NH-aryl, NHCHO, NHC(O)-alkyl, NHC(O)-aryl, NH-cycloalkyl; and NH-heterocyclyl.

The present invention also provides the process for preparing products of formula (I).

The products according to the invention can be prepared on the basis of conventional methods of organic chemistry. Scheme 1 below is illustrative of a method which is used for preparing example 6. In this context it does not constitute any limitation on the scale of the invention, as far as concerns the methods of preparing the compounds claimed.

-Scheme 1-

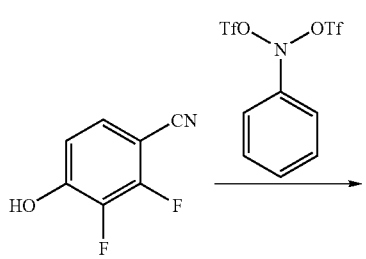

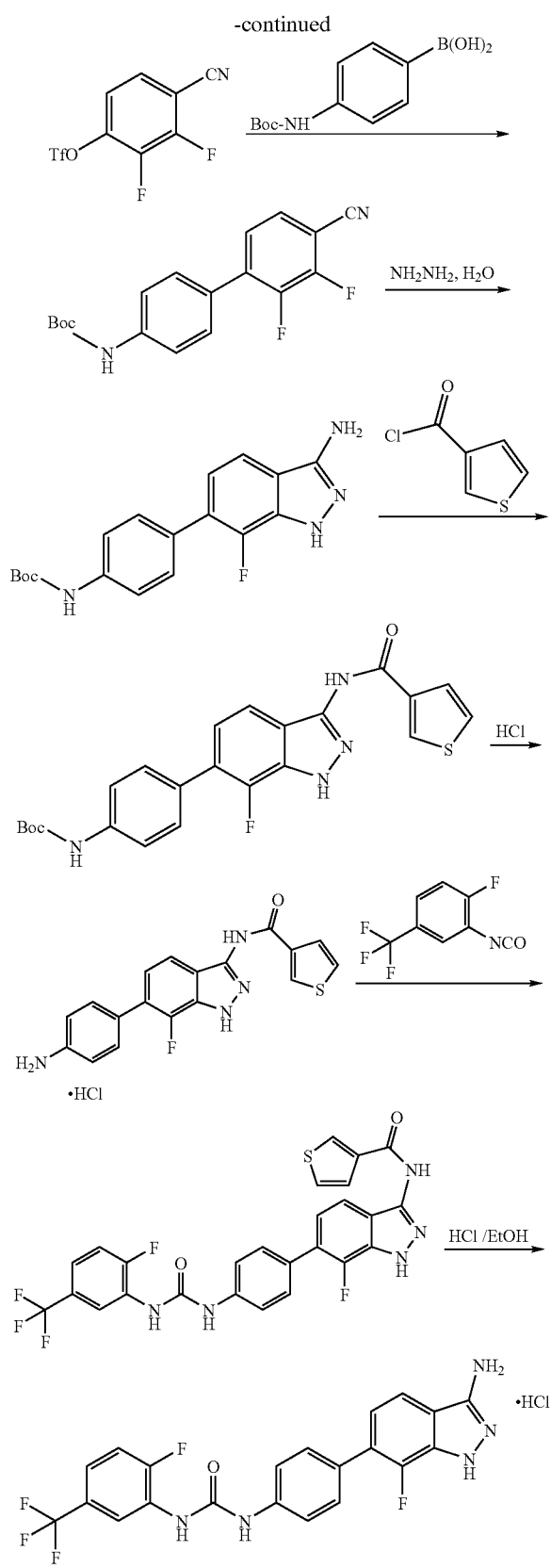

-continued

It is understood for the skilled worker that, in order to implement the processes according to the invention that are described above, it may be necessary to introduce protective groups for the amino, carboxyl, and alcohol functions in order to avoid side reactions. These groups are groups which can be removed without affecting the remainder of the molecule. Examples of protective groups for the amino function include tert-butyl carbamate, which can be regenerated by means of iodotrimethylsilane; acetyl, which can be regenerated in an acidic medium (hydrochloric acid, for example). Possible protective groups for the carboxyl function include the esters (methoxymethyl ester, benzyl ester, for example). Possible protective groups for the alcohol function include the esters (benzoyl ester, for example), which can be regenerated in an acidic medium or by catalytic hydrogenation. Other protective groups that can be used are described by T. W. Greene et al. in Protective Groups in Organic Synthesis, third edition, 1999, Wiley-Interscience.

The compounds of formula (I) are isolated and can be purified by the usual known methods, such as by crystallization, chromatography or extraction, for example.

The enantiomers and diastereoisomers of the compounds of formula (I) also form part of the invention.

Compounds of formula (I) comprising a basic residue may be optionally converted to addition salts with an organic or inorganic acid, by the action of such an acid within a solvent, for example an organic solvent such as an alcohol, a ketone, an ether or a chlorinated solvent.

The compounds of formula (I) comprising an acidic residue may be optionally converted to metal salts or to addition salts with nitrogenous bases in accordance with methods which are known per se. These salts can be obtained by the action of a metal base (alkali metal or alkaline earth metal base, for example), ammonia, an amine or an amine salt on a compound of formula (I), in a solvent. The salt formed is separated by customary methods.

These salts also form part of the invention.

When a product according to the invention exhibits at least one free basic function, pharmaceutically acceptable salts can be prepared by reacting said product with an organic or inorganic acid. Pharmaceutically acceptable salts include chlorides, nitrates, sulfates, hydrogen sulfates, pyrosulfates, bisulfates, sulfites, bisulfites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulfonates, propanesulfonates, xylenesulfonates, salicylates, cinnamates, glutamates, aspartates, glucuronates, and galacturonates.

When a product according to the invention exhibits at least one free acidic function, pharmaceutically acceptable salts may be prepared by reacting said product with an organic or inorganic base. Pharmaceutically acceptable bases include hydroxides of alkali metal or alkaline earth metal cations, such as Li, Na, K, Mg and Ca, and basic amine compounds such as ammonia, arginine, histidine, piperidine, morpholine, piperazine, and triethylamine.

The products according to the invention which are prepared in the form of salts, particularly in a hydrochloride form, may be brought out of the salt form by the action of an organic or inorganic base in accordance with known techniques.

The invention is also described by the examples below, which are given by way of illustration of the invention.

The LC/MS analyses were carried out on a Micromass model LCT instrument connected to an HP 1100 device. The abundance of the products was measured by means of an HP G1315A diode array detector over a wavelength range of 200-600 nm and a Sedex 65 light scattering detector. The mass spectra were acquired over a range from 180 to 800. The data were analyzed using the Micromass MassLynx software. Separation was performed on a Hypersil BDS C18 column, 3 µm (50×4.6 mm), eluting with a linear gradient from 5% to 90% of acetonitrile containing 0.05% (v/v) of trifluoroacetic acid (TFA) in water containing 0.05% (v/v) TFA over 3.5 minutes at a flow rate of 1 mL/min. The total analysis time, including the period for re-equilibrating the column, is 7 minutes.

The MS spectra were carried out using electrospray (ES$^+$) technique on a Platform II (Micromass) instrument. The principal ions observed are described.

The melting points were measured using the capillary technique on a Mettler FP62 instrument, range 30° C. to 300° C., with a rise of 2° C. per minute.

Purification by LC/MS:

The products can be purified by LC/MS, using a Waters FractionsLynx system composed of a Waters model 600 gradient pump, a Waters model 515 regeneration pump, a Waters Reagent Manager dilution pump, a Waters model 2700 autoinjector, two Rheodyne LabPro model valves, a Waters model 996 diode array detector, a Waters model ZMD mass spectrometer and a Gilson model 204 fraction collector. The system was controlled by the Waters FractionLynx software. Separation was carried out alternately on two Waters Symmetry columns (C$_{18}$, 5 µM, 19×50 mm, catalogue reference 186000210), one column undergoing regeneration with a 95/5 (v/v) water/acetonitrile mixture containing 0.07% (v/v) of trifluoroacetic acid while the other column was in separation service. The columns were eluted using a linear gradient from 5% to 95% of acetonitrile containing 0.07% (v/v) of trifluoroacetic acid in water containing 0.07% (v/v) of trifluoroacetic acid, at a flow rate of 10 mL/min. At the exit from the separation column, one thousandth of the effluent is separated by means of an LC Packing Accurate, diluted with methyl alcohol at a flow rate of 0.5 mL/min and sent to the detectors, in a proportion of 75% to the diode array detector and the remaining 25% to the mass spectrometer. The remainder of the effluent (999/1000) is sent to the fraction collector, where the flow is discarded until the mass of the expected product is detected by the FractionLynx software. The molecular formulae of the expected products are supplied to the FractionLynx software, which actuates the collection of the product when the mass signal detected corresponds to the ion [M+H]$^+$ and/or to [M+Na]$^+$. In certain cases, depending on the results of analytical LC/MS, when an intense ion corresponding to [M+2H]$^{++}$ has been detected, the value corresponding to half the calculated molecular mass (MW/2) is also supplied to the FractionLynx software. Under these conditions, collection is also actuated when the mass signal of the ion [M+2H]$^{++}$ and/or [M+Na+H]$^{++}$ are detected. The products were collected in tared glass tubes. Following collection, the solvents were evaporated in a Savant AES 2000 or Genevac HT8 centrifugal evaporator and the masses of products were determined by weighing the tubes following evaporation of the solvents.

EXAMPLE 1

1-[4-(3-Amino-1H-indazol-6-yl)phenyl]-3-(2-fluoro-5-trifluoromethylphenyl)urea hydrochloride

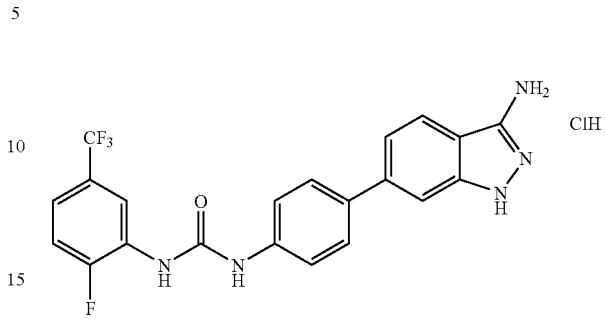

1-[4-(3-Aminofluoro-1H-indazol-6-yl)phenyl]-3-(2-fluoro-5-trifluoromethylphenyl)urea hydrochloride is obtained by hydrolyzing 0.4 g of 1-(4-{3-[(thiophen-3-yl)carbonylamino]-1H-indazol-6-yl}phenyl)-3-(2-fluoro-5-trifluoromethylphenyl)urea with 37% hydrochloric acid (4.2 mL) in ethanol at reflux for 24 hours. The reaction mixture is concentrated under reduced pressure, to give a residue which is stirred with 10 mL of acetonitrile and then recrystallized hot from 7 mL of methanol. Filtration and drying under vacuum give 70 mg of 1-[4-(3-amino-1H-indazol-6-yl)phenyl]-3-(2-fluoro-5-trifluoromethylphenyl)urea hydrochloride, whose characteristics are as follows:

IR spectrum (KBr): 3413; 1656; 1550; 1442; 1340; 1117 & 816 cm$^{-1}$ $^1$H NMR spectrum (400 MHz, (CD$_3$)$_2$SO, δ in ppm): from 7.38 to 7.45 (m, 2H); from 7.49 to 7.56 (m, 2H); 7.60 (broad d, J=8.5 Hz, 2H); 7.70 (broad d, J=8.5 Hz, 2H); 7.90 (d, J=8.5 Hz, 1H); 8.65 (broad dd, J=2.5 and 7.5 Hz, 1H); 8.98 (broad d, J=2.0 Hz, 1H); 9.42 (s, 1H).

MS spectrum (ES$^+$): m/z=430 [MH$^+$]

1-(4-{3-[(Thiophen-3-yl)carbonylamino]-1H-indazol-6-yl}phenyl)-3-(2-fluoro-5-trifluoromethylphenyl)urea A solution of 1.72 g of 6-(4-aminophenyl)-3-[(thiophen-3-yl)carbonylamino]-1H-indazole hydrochloride and 0.65 mL of triethylamine in 70 mL of tetrahydrofuran is admixed slowly under an argon atmosphere with 0.67 mL of 2-fluoro-5-trifluoromethylphenyl isocyanate. The reaction mixture is stirred at 24° C. for 3.5 hours and then concentrated under reduced pressure. The residue is purified by flash chromatography on a silica column (60; 35-70 µM), eluting with a dichloromethane/methanol (97/3 by volume) mixture, to give 0.4 g of 1-(4-{3-[(thiophen-3-yl)carbonylamino]-1H-indazol-6-yl}phenyl)-3-(2-fluoro-5-trifluoromethylphenyl)urea, whose characteristics are as follows:

MS spectrum (ES$^+$): m/z=540 [MH$^+$]

6-(4-Aminophenyl)-3-[(thiophen-3-yl)carbonylamino]-1H-indazole hydrochloride

A solution of 4.2 g of 6-(4-tert-butoxycarbonylaminophenyl)-1-[3-(thiophen-3-yl)carbonylamino]-1H-indazole in 30 mL of methanol is admixed with 12 mL of 4N hydrochloric dioxane. The reaction mixture is stirred for 14 hours at a temperature in the region of 20° C. and then is concentrated under reduced pressure. The solid residue is stirred with 25 mL of isopropyl ether filtered and treated with suction, to give 3.45 g of 6-(4-aminophenyl)-1-[3-[(thiophen-3-yl)carbonylamino]-1H-indazole hydrochloride, whose characteristics are as follows:

MS spectrum (ES+): m/z=335 [MH+]

6-(4-tert-Butoxycarbonylaminophenyl)-1-[3-(thiophen-3-yl)carbonylamino]-1H-indazole A solution of 6 g of 6-bromo-1-[(thiophen-3-yl)carbonyl]-3-[(thiophen-3-yl)carbonylamino]indazole in 350 mL of dioxane is admixed with 4.93 g of 4-(tert-butyloxycarbonylamino)phenylboronic acid. A solution of 4.12 g of sodium carbonate in 90 mL of water is added, followed by 1.93 g of tetrakistriphenylphosphinepalladium. The reaction mixture is stirred at 90° C. for 4 hours and then poured into 120 mL of distilled water. Following extraction with ethyl acetate and then washing of the extracts with saturated sodium chloride solution, the organic phase is concentrated under reduced pressure, to give 13.18 g of a solid, which is purified by flash chromatography on a silica column (60; 35-70 µM), eluting with a cyclohexane/ethyl acetate (60/40 by volume) mixture, to give 4.2 g of 6-(4-tert-butoxycarbonylaminophenyl)-1-[3-(thiophen-3-yl)carbonylamino]-1H-indazole, whose characteristics are as follows:

MS spectrum (ES+): m/z=435 [MH+]

6-Bromo-1-[(thiophen-2-yl)carbonyl]-3-[(thiophen-2-yl)carbonylamino]indazole

A solution of 10 g of 6-bromo-3-amino-1H-indazole in 250 mL of pyridine is admixed with 13.8 g of 3-thiophenecarboxylic chloride. The reaction mixture is stirred under an argon atmosphere for 16 hours at a temperature close to 25° C. and then poured into 400 mL of water. The suspension is then filtered and the product is washed with 2×80 mL of water, treated with suction and dried, to give 19.27 g of 6-bromo-1-[(thiophen-2-yl)carbonyl]-3-[(thiophen-2-yl)carbonylamino]indazole, whose characteristics are as follows:

MS spectrum (ES+): m/z=433 [MH+]

6-Bromo-3-amino-1H-indazole

A solution of 10 g of 4-bromo-2-fluorobenzonitrile in 300 mL of ethanol is admixed with 7.29 mL of hydrazine hydrate. The reaction mixture is stirred for 22 hours at reflux and then concentrated under reduced pressure. The residue obtained is stirred for 30 minutes in 200 mL of distilled water. The suspended solid is isolated by filtration, washed with water and treated with suction. After drying under vacuum, 10 g of 6-bromo-3-amino-1H-indazole are obtained, whose characteristics are as follows:

MS spectrum (ES+): m/z=213 [MH+]
Melting point: 249° C.

EXAMPLE 2

1-[4-(3-Amino-1H-indazol-6-yl)phenyl]-2,3-dichlorobenzenesulfonamide hydrochloride

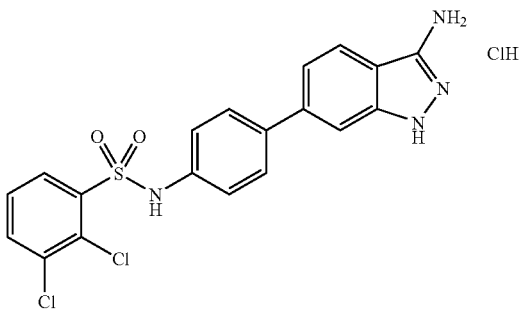

1-[4-(3-Amino-1H-indazol-6-yl)phenyl]-2,3-dichlorobenzenesulfonamide hydrochloride is obtained by hydrolyzing 0.54 g of 3-thiophenecarboxylic acid {6-[4-(2,3-dichlorobenzenesulfonylamino)phenyl]-1H-indazol-3-yl}amide with 37% hydrochloric acid (5 mL) in 40 mL of ethanol at reflux for 24 hours. The reaction mixture is concentrated under reduced pressure, to give a residue which is stirred with 10 mL of acetonitrile. Filtration and washing with 10 mL of isopropyl ether produce 0.46 g of 1-[4-(3-amino-1H-indazol-6-yl)phenyl]-2,3-dichlorobenzenesulfonamide hydrochloride, whose characteristics are as follows:
 IR spectrum (KBr): 3426; 3134; 2902; 2711; 1659; 1404; 1164; 924; 705 & 593 cm$^{-1}$
 $^1$H NMR spectrum (400 MHz, (CD$_3$)$_2$SO, δ in ppm): 7.21 (broad d, J=9.0 Hz, 2H); 7.29 (broad d, J=9.0 Hz, 1H); 7.44 (broad s, 1H); 7.58 (t, J=7.5 Hz, 1H); 7.62 (broad d, J=9.0 Hz, 2H); 7.85 (d, J=9.0 Hz, 1H); 7.93 (dd, J=1.5 and 7.5 Hz, 1H); 8.09 (dd, J=1.5 and 7.5 Hz, 1H); 10.95 (broad s, 1H); from 11.9 to 12.4 (highly spread-out m, 1H).
 MS spectrum (ES+): m/z=433 [MH+]

EXAMPLE 3

3-Thiophenecarboxylic acid {6-[4-(2,3dichlorobenzenesulfonylamino)phenyl]-1H-indazol-3-yl}amide A solution of 1.72 g of 6-(4-aminophenyl)-3-[(thiophen-3-yl)carbonylamino]-1H-indazole hydrochloride in 69 mL of pyridine is admixed at 0° C. with a solution of 1.14 g of 2,3-dichlorobenzenesulfonyl chloride in 23 mL of dichloromethane. The reaction mixture is stirred for 3 hours at a temperature in the region of 20° C. and then concentrated under reduced pressure. The dry residue is diluted in ethyl acetate, washed with water and then washed with saturated sodium chloride solution and concentrated under reduced pressure. The foam obtained is purified by flash chromatography, eluting with a dichloromethane/methanol/acetonitrile (96/2/2 by volume) mixture, to give 0.69 g of 3-thiophenecarboxylic acid {6-[4-(2,3-dichlorobenzenesulfonylamino)phenyl]-1H-indazol-3-yl}amide, whose characteristics are as follows:

IR spectrum (KBr): 3388; 3274; 3107; 1656; 1528; 1404; 1268; 1167; 737; 705 & 598 cm$^{-1}$ $^1$H NMR spectrum (400 MHz, (CD$_3$)$_2$SO, δ in ppm): 7.20 (broad d, J=8.5 Hz, 2H); 7.29 (dd, J=2.5 and 9.0 Hz, 1H); from 7.52 to 7.59 (m, 2H); 7.62 (broad d, J=8.5 Hz, 2H); 7.67 (dd, J=2.5 and 5.0 Hz, 1H); 7.71 (dd, J=1.5 and 5.0 Hz, 1H); 7.78 (d, J=9.0 Hz, 1H); 7.92 (dd, J=1.5 and 7.5 Hz, 1H); 8.09 (dd, J=1.5 and 7.5 Hz, 1H); 8.44 (dd, J=1.5 and 2.5 Hz, 1H); 10.65 (broad s, 1H); 10.9 (spread-out m, 1H); 12.8 (broad s, 1H).

Melting point: 196° C.

MS spectrum (EI): m/z=542 [M$^{+o}$]

EXAMPLE 4

6-(4-Aminophenyl)-7-fluoro-3-[(thiophen-3-yl)carbonylamino]-1H-indazole hydrochloride

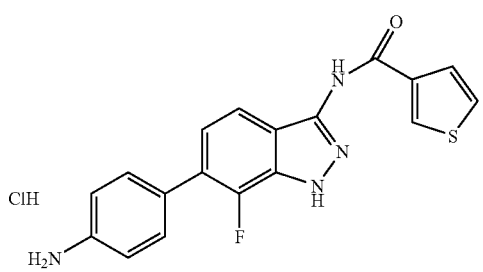

A solution of 0.63 g of 6-(4-tert-butoxycarbonylaminophenyl)-1-[3-(thiophen-3-yl)carbonylamino]-7-fluoro-1H-indazole in 20 mL of methanol is admixed with 1.74 mL of 4N hydrochloric dioxane. The reaction mixture is stirred for 14 hours at a temperature in the region of 20° C. and then concentrated under reduced pressure. The solid residue is stirred with 10 mL of isopropyl ether, isolated by filtration and treated with suction to give 0.52 g of 6-(4-aminophenyl)-1-[3-[(thiophen-3-yl)carbonylamino]-7-Fluoro-1H-indazole hydrochloride, whose characteristics are as follows:

IR spectrum (KBr) 2932; 1728; 1607; 1519; 1504; 1432; 1380; 1288; 1194; 1091; 914; 758 and 701 cm$^{-1}$ $^1$H NMR spectrum (400 MHz, (CD$_3$)$_2$SO, δ in ppm): 7.18 (dd, J=7.5 and 8.5 Hz, 1H); 7.33 (broad d, J=8.5 Hz, 2H); from 7.62 to 7.76 (m, 5H); 8.49 (m, 1H); 10.9 (s, 1H); from 13.3 to 13.6 (very spread-out m, 1H)

6-(4-tert-Butoxycarbonylaminophenyl)-1-[3-(thiophen-3-yl)carbonylamino]-7-fluoro-1H-indazole A solution of 0.54 g of 6-(4-tert-butoxycarbonylaminophenyl)-3-amino-7-fluoro-1H-indazole in 10 mL of pyridine is admixed at 15° C. with 0.23 g of 3-chlorocarbonylthiophene. The reaction mixture is stirred for 12 hours at a temperature in the region of 20° C. and then diluted in 50 mL of dichloromethane and washed with 4×50 mL of distilled water. The organic phase is then concentrated under reduced pressure. The solid residue obtained is stirred with 10 mL of isopropyl ether, filtered and treated with suction, to give 0.63 g of 6-(4-aminophenyl)-1-[3-[(thiophen-3-yl)-carbonylamino]-7-fluoro-1H-indazole, whose characteristics are as follows:

IR spectrum (KBr): 3248; 2977; 1723; 1658; 1591; 1533; 1342; 1238; 1160; 1052 and 805 cm$^{-1}$ $^1$H NMR spectrum (400 MHz, (CD$_3$)$_2$SO, δ in ppm): 1.52 (s, 9H); 7.17 (dd, J=6.5 and 8.5 Hz, 1H); 7.56 (broad d, J=8.5 Hz, 2H); from 7.59 to 7.65 (m, 3H); 7.70 (dd, J=3.0 and 5.0 Hz, 1H); 7.74 (dd, J=1.5 and 5.0 Hz, 1H); 8.50 (dd, J=1.5 and 3.0 Hz, 1H); 9.52 (s, 1H); 10.8 (s, 1H); 13.4 (broad s, 1H)

3-Amino-7-fluoro-6-(4-tert-butoxycarbonylaminophenyl)-1H-indazole

A solution of 0.8 g of 2,3-difluoro-4-(4-tert-butoxycarbonylaminophenyl)benzonitrile in 25 mL of absolute ethanol is admixed with 0.35 mL of hydrazine hydrate. The reaction mixture is stirred for 19 hours at the reflux of the solvent and then concentrated under reduced pressure. The solid residue is stirred with 25 mL of distilled water, filtered and washed with 2×5 mL of dichloromethane. After suction treatment, 0.54 g of 3-amino-7-fluoro-6-(4-tert-butoxycarbonylaminophenyl)-1H-indazole is obtained, whose characteristics are as follows:

IR spectrum (KBr): 3422; 3374; 2981; 1732; 1612; 1530; 1368; 1222; 1159; 1050; 844 and 806 cm$^{-1}$ $^1$H NMR spectrum (400 MHz, (CD$_3$)$_2$SO, δ in ppm): 1.52 (s, 9H); 5.50 (s, 2H); 6.98 (dd, J=6.5 and 8.5 Hz, 1H); from 7.48 to 7.61 (m, 5H); 9.48 (s, 1H); 11.9 (broad s, 1H)

2,3-Difluoro-4-(4-tert-butoxycarbonylaminophenyl) benzonitrile

A solution of 2,3-difluoro-4-trifluoromethylsulfonyloxybenzonitrile in 60 mL of dioxane is admixed under an argon atmosphere with 1.24 g of 4-(tert-butyloxycarbonylamino) phenylboronic acid. A solution of 1.03 g of sodium carbonate in 15 mL of water is added, followed by 0.48 g of tetrakistriphenylphosphinepalladium. The reaction mixture is stirred at 90° C. for 3 hours and then poured into 80 mL of distilled water. Following extraction with ethyl acetate and then washing with saturated sodium chloride solution, the organic phase is concentrated under reduced pressure, to give 0.8 g of 2,3-difluoro-4-(4-tert-butoxycarbonylaminophenyl) benzonitrile, whose characteristics are as follows:

IR spectrum (KBr): 3345; 2981; 2247; 1719; 1595; 1532; 1470; 1409; 1325; 1239; 1158; 1057; 898; 825; 665 and 522 cm$^{-1}$ MS spectrum (ES$^+$): m/z=331 [MH$^+$]

2,3-Difluoro-4-trifluoromethylsulfonyloxybenzonitrile

A solution of 2 g of 2,3-difluoro-4-hydroxybenzonitrile in 20 mL of dimethylformamide is admixed with 0.43 g of sodium hydride in small portions. After 10 minutes of stirring at ambient temperature, 4.84 g of N-phenyltrifluoromethanesulfonimide are added. After 10 hours of stirring at a temperature in the region of 20° C., the reaction mixture is poured into 100 mL of distilled water and extracted with ethyl acetate. The organic phase is washed with saturated sodium chloride solution and then concentrated under reduced pressure, to give 3.68 g of an oil which is purified by flash chromatography on a silica column (60; 35-70 μM), eluting with a cyclohexane/ethyl acetate (92/8 by volume) mixture; 0.52 g of 2,3-difluoro-4-trifluoromethylsulfonyloxybenzonitrile is obtained, whose characteristics are as follows:

IR spectrum (KBr): 2245; 1497; 1442; 1232; 1138; 1035; 960; 834 and 603 cm$^{-1}$ MS spectrum (ES$^+$): m/z=288 [MH$^+$]

EXAMPLE 5

3-Thiophenecarboxylic acid {6-[4-(2,3-dichlorobenzenesulfonylamino)-7-fluorophenyl]-1H-indazol-3-yl}amide

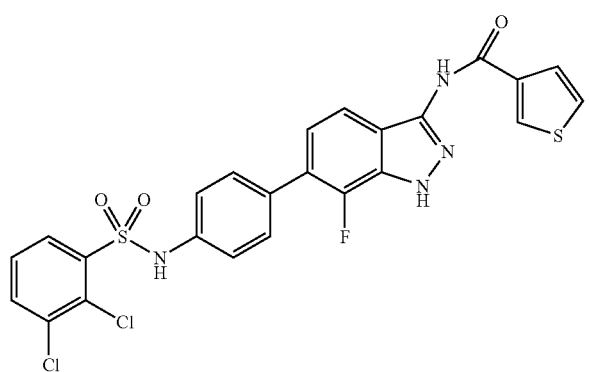

A solution of 6-(4-aminophenyl)-7-fluoro-3-[(thiophen-3-yl)carbonylamino]-1H-indazole hydrochloride in 20 mL of pyridine is added at 0° C. to a solution of 0.315 g of 2,3-dichlorobenzenesulfonyl chloride in 6.5 mL of dichloromethane. The reaction mixture is stirred for 16 hours at a temperature in the region of 20° C. and then concentrated under reduced pressure. The dry residue is diluted in dichloromethane, washed with water and with saturated sodium chloride solution and then concentrated under reduced pressure. The foam obtained is purified by flash chromatography, eluting with a dichloromethane/methanol/acetonitrile (96/2/2 by volume) mixture, to give 0.2 g of 3-thiophenecarboxylic acid {6-[4-(2,3-dichlorobenzenesulfonylamino)-7-fluorophenyl]-1H-indazol-3-yl}amide, whose characteristics are as follows:

IR spectrum (KBr): 3421; 1659; 1527; 1405; 1340; 1166; 1091; 913; 739; 705 and 598 cm$^{-1}$ $^1$H NMR spectrum (400 MHz, (CD$_3$)$_2$SO, δ in ppm): 7.10 (dd, J=6.5 and 8.5 Hz, 1H); 7.21 (broad d, J=8.5 Hz, 2H); 7.51 (broad d, J=8.5 Hz, 2H); from 7.53 to 7.62 (m, 2H); 7.67 (dd, J=2.5 and 5.0 Hz, 1H); 7.71 (dd, J=1.5 and 5.0 Hz, 1H); 7.92 (broad d, J=7.5 Hz, 1H); 8.10 (dd, J=1.5 and 7.5 Hz, 1H); 8.46 (dd, J=1.5 and 2.5 Hz, 1H); 10.75 (broad s, 1H); 11.0 (spread-out m, 1H); 13.35 (broad s, 1H).

MS spectrum (EI): m/z=560 [M$^{+o}$]

EXAMPLE 6

1-(4-{7-Fluoro-3-[(thiophen-3-yl)carbonylamino]-1H-indazol-6-yl}phenyl)-3-(2-fluoro-5-trifluoromethylphenyl)urea A solution of 0.88 g of 6-(4-aminophenyl)-7-fluoro-1-[3-[(thiophen-3-yl)carbonylamino]-1H-indazole hydrochloride in 80 mL of tetrahydrofuran is admixed with 0.46 g of 2-fluoro-5-trifluoromethylphenyl isocyanate and 0.636 mL of triethylamine. The reaction mixture is stirred for 12 hours at a temperature in the region of 20° C. and then concentrated under reduced pressure. Purification by flash chromatography on a silica column (60; 35-70 μM), eluting with a dichloromethane/acetonitrile/methanol (96/2/2 by volume) mixture, gives 0.51 g of 1-(4-{7-fluoro-3-[(thiophen-3-yl)carbonylamino]-1H -indazol-6-yl}phenyl)-3-(2-fluoro-5-trifluoromethylphenyl)urea, whose characteristics are as follows:

IR spectrum (KBr): 3418; 1659; 1608; 1542; 1442; 1339; 1264; 1200; 1122; 741 and 614 cm$^{-1}$ $^1$H NMR spectrum (400 MHz, (CD$_3$)$_2$SO, δ in ppm): 7.20 (dd, J=7.5 and 9.0 Hz, 1H); 7.42 (m, 1H); 7.53 (dd, J=9.0 and 10.5 Hz, 1H); from 7.60 to 7.72 (m, 6H); 7.74 (dd, J=1.0 and 5.0 Hz, 1H); 8.49 (dd, J=1.0 and 3.0 Hz, 1H); 8.65 (dd, J=2.5 and 7.5 Hz, 1H); 9.04 (broad m, 1H); 9.44 (broad s, 1H); 10.8 (broad s, 1H); 13.4 (very broad s, 1H).

EXAMPLE 7

1-[4-(3-Amino-7-fluoro-1H-indazol-6-yl)phenyl]-3-(2-fluoro-5-trifluoro-methylphenyl)urea hydrochloride 1-[4-(3-Amino-7-fluoro-1H-indazol-6-yl)phenyl]-3-(2-fluoro-5-trifluoromethylphenyl)urea hydrochloride is obtained by hydrolyzing 1-(4-{7-fluoro-3-[(thiophen-3-yl)carbonylamino]-1H-indazol-6-yl}phenyl)-3-(2-fluoro-5-trifluoromethylphenyl)urea with 37% hydrochloric acid (4.2 mL) in ethanol at reflux for 24 hours. The reaction mixture is concentrated under reduced pressure, to give a residue which is stirred with 15 mL of acetonitrile. Filtration and drying under vacuum gives 0.38 g of 1-[4-(3-amino-7-fluoro-1H-indazol-6-yl)phenyl]-3-(2-fluoro-5-trifluoromethylphenyl) urea hydrochloride, whose characteristics are as follows:

IR spectrum (KBr): 3327; 3168; 1653; 1601; 1544; 1443; 1342; 1322; 1187; 1117; 1070; 809 and 615 cm$^{-1}$ $^1$H NMR spectrum (400 MHz, (CD$_3$)$_2$SO, δ in ppm): 7.08 (dd, J=6.5 and 8.0 Hz, 1H); 7.42 (m, 1H); from 7.49 to 7.65 (m, 6H); 8.65 (dd, J=2.5 and 7.0 Hz, 1H); 8.99 (d, J=3.5 Hz, 1H); 9.40 (s, 1H); from 11.8 to 12.5 (very spread-out m), 1H.

EXAMPLE 8

1-[4-(3-Amino-1H-indazol-6-yl)-7-fluorophenyl]-2,3-dichlorobenzenesulfonamide hydrochloride

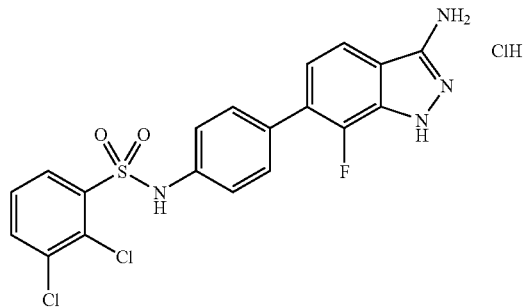

1-[4-(3-Amino-1H-indazol-6-yl)-7-fluorophenyl]-2,3-dichlorobenzenesulfonamide hydrochloride is obtained by hydrolyzing 0.15 g of 3-thiophenecarboxylic acid {6-[4-(2,3-dichlorobenzenesulfonylamino)-7-fluorophenyl]-1H-indazol-3-yl}amide with 37% hydrochloric acid (1.36 mL) in 11 mL of ethanol at reflux for 16 hours. The reaction mixture is concentrated under reduced pressure, to give a residue which is stirred with 5 mL of acetonitrile. Filtration gives 90 mg of 1-[4-(3-amino-1H-indazol-6-yl)-7-fluorophenyl]-2,3-dichlorobenzenesulfonamide hydrochloride, whose characteristics are as follows:

IR spectrum (KBr): 3435; 1656; 1507; 1404; 1164; 1139; 912; 704 & 593cm$^{-1}$ $^1$H NMR spectrum (400 MHz, (CD$_3$)$_2$SO, δ in ppm): 7.00 (dd, J=6.5 and 8.5 Hz, 1H); 7.22 (broad d, J=8.5 Hz, 2H); 7.50 (broad d, J=8.5 Hz, 2H); from 7.54 to 7.62 (m, 2H); 7.94 (dd, J=1.5 and 7.5 Hz, 1H); 8.10 (dd, J=1.5 and 7.5 Hz, 1H); 11.0 (broad s, 1H).

MS spectrum (EI): m/z=450 [M$^{+°}$]

EXAMPLE 9

1-(4-{4,5,7-Trifluoro-3-[(thiophen-3-yl)carbonylamino]-1H-indazol-6-yl}-phenyl)-3-(2-fluoro-5-trifluoromethylphenyl)urea

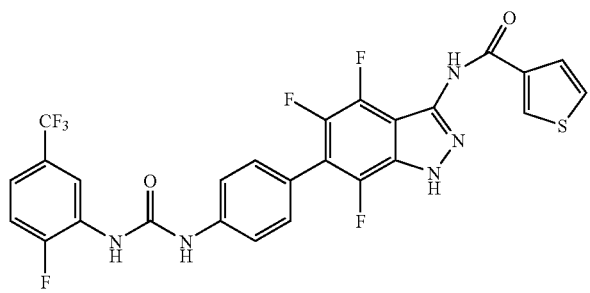

A solution of 0.175 g of 6-(4-aminophenyl)-4,5,7-trifluoro-1-[3-[(thiophen-3-yl) -carbonylamino]-1H-indazole hydrochloride in 10 mL of tetrahydrofuran is admixed with 84.5 mg of 2-fluoro-5-trifluoromethylphenyl isocyanate and 58 μL of triethylamine. The reaction mixture is stirred for 16 hours at a temperature in the region of 20° C. and then concentrated under reduced pressure. The residue obtained is stirred in 15 mL of ethyl acetate and then filtered and treated with suction to give 29 mg of 1-(4-{4,5,7-trifluoro-3-[(thiophen-3-yl)-carbonylamino]-1H-indazol-6-yl}phenyl)-3-(2-fluoro-5-trifluoro -methylphenyl)urea, whose characteristics are as follows:

IR spectrum (KBr) 3288; 1686; 1635; 1535; 1440; 1319; 1126 & 992cm$^{-1}$ $^1$H NMR spectrum (400 MHz, (CD$_3$)$_2$SO, δ in ppm): 7.41 (m, 1H); from 7.48 to 7.57 (m, 3H); from 7.60 to 7.70 (m, 4H); 8.41 (broad s, 1H); 8.63 (broad d, J=7.5 Hz, 1H); 9.01 (broad m, 1H); 9.43 (broad s, 1H); 10.6 (spread-out m, 1H); from 13.6 to 14.0 (very spread-out m, 1H)

MS spectrum (ES$^+$): m/z=594 [MH$^+$]

6-(4-Aminophenyl)-4,5,7-trifluoro-1-[3-[(thiophen-3-yl)carbonylamino]-1H-indazole hydrochloride A solution of 0.65 g of 6-(4-tert-butoxycarbonylaminophenyl)-1-[3-(thiophen-3-yl)carbonylamino]-4,5,7-trifluoro-1H-indazole in 10 mL of methanol is admixed with 1.66 mL of 4N hydrochloric dioxane. The reaction mixture is stirred for 48 hours at a temperature in the region of 20° C., then filtered and treated with suction to give 0.21 g of 6-(4-aminophenyl)-1-[3-[(thiophen-3-yl)carbonylamino]-4,5,7-trifluoro-1H-indazole hydrochloride, whose characteristics are as follows:

MS spectrum (ES$^+$): m/z=389 [MH$^+$]

6-(4-tert-Butoxycarbonylaminophenyl)-1-[3-(thiophen-3-yl)carbonylamino]-4,5,7-trifluoro-1H-indazole A solution of 0.5 g of 6-bromo-1-[3-[(thiophen-3-yl)carbonylamino]-4,5,7-trifluoro-1H -indazole in 40 mL of dioxane is admixed with 0.31 g of 4-(tert -butyloxycarbonylamino)phenylboronic acid. A solution of 0.42 g of sodium carbonate in 5 mL of water is added, followed by 0.184 g of tetrakistriphenylphosphinepalladium. The reaction mixture is stirred at 90° C. for 42 hours and then poured into 40 mL of distilled water. Following extraction with dichloromethane and then washing with saturated sodium chloride solution, the organic phase is concentrated under reduced pressure, to give a solid which is purified by flash chromatography on a silica column (60; 35-70 μM), eluting with a cyclohexane/ethyl acetate (50/50 by volume) mixture, to give 0.65 g of 6-(4-tert-butoxycarbonylaminophenyl)-1-[3-(thiophen-3-yl)carbonylamino]-4,5,7-trifluoro-1H-indazole, whose characteristics are as follows:

MS spectrum (ES$^+$): m/z=489 [MH$^+$]

6-Bromo-1-[3-[(thiophen-3-yl)carbonylamino]-4,5,7-trifluoro-1H-indazole

A solution of 1.8 g of 6-bromo-1-[(thiophen-3-yl)carbonyl]-3-[(thiophen-3-yl)carbonylamino]-4,5,7-trifluoroindazole in 130 mL of dioxane is added to 1.1 g of sodium carbonate in solution in 45 mL of water. The reaction mixture is heated at 90° C. for 4 hours and then concentrated under reduced pressure, to give a solid which is purified by flash chromatography on a silica column (60; 35-70 μM), eluting with a cyclohexane/ethyl acetate (85/15 by volume) mixture to give 0.32 g of 6-bromo-1-[3-[(thiophen-3-yl)carbonylamino]-4,5,7-trifluoro-1H-indazole, whose characteristics are as follows:

MS spectrum (ES⁺): m/z=377 [MH⁺]

6-Bromo-1-[(thiophen-3-yl)carbonyl]-3-[(thiophen-3-yl)carbonylamino]-4,5,7-trifluoroindazole A solution of 3 g of 6-bromo-3-amino-4,5,7-1H-indazole in 60 mL of pyridine is admixed with 3.3 g of thiophene-3-carboxylic chloride. The reaction mixture is stirred under an argon atmosphere for 16 hours at a temperature close to 25° C. and then poured into 120 mL of water. The suspension is washed with 2×100 mL of dichloromethane and then filtered, treated with suction and dried, to give 1.85 g of 6-bromo-1-[(thiophen-3-yl)carbonyl]-3-[(thiophen-3-yl)carbonylamino]-4,5,7-trifluoroindazole, whose characteristics are as follows:

MS spectrum (ES⁺): m/z=487 [MH⁺]

6-Bromo-3-amino-4,5,7-1H-indazole

A solution of 5 g of 4-bromo-2,3,5,6-tetrafluorobenzonitrile in 90 mL of ethanol is admixed with 9.7 mL of hydrazine hydrate. The reaction mixture is stirred for 17 hours at reflux and then concentrated under reduced pressure. The residue obtained is stirred for 30 minutes in 80 mL of distilled water. The suspended solid is isolated by filtration, washed with water, treated with suction and then triturated in 200 mL of ethyl ether and isolated by filtration, to give 1.03 g of 6-bromo-3-amino-4,5,7-1H-indazole, whose characteristics are as follows:

MS spectrum (ES⁺): m/z=267 [MH⁺]

EXAMPLE 10

1-(4-[3-[(Thiophen-3-yl)carbonylamino]-1H-indazol-6-yl}phenyl)-3-(2-fluoro-5-trifluoromethylphenyl)urea

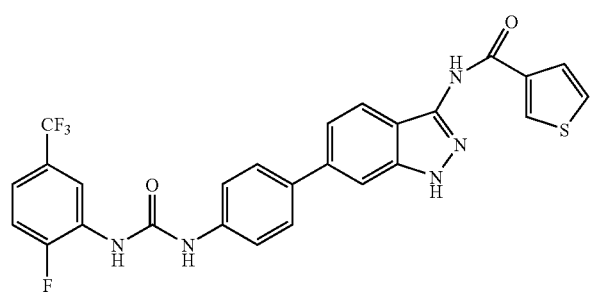

Working in accordance with the procedure described in example 1, 1-(4-{3-[(thiophen-3-yl)carbonylamino]-1H-indazol-6-yl}phenyl)-3-(2-fluoro-5-trifluoromethylphenyl)urea is obtained in the form of a yellow solid, whose characteristics are as follows:

IR spectrum (KBr): 3406; 1656; 1536; 1441; 1339; 1265; 1118 & 808 cm⁻¹

¹H NMR spectrum (400 MHz, (CD₃)₂SO, δ in ppm): 7.39 (dd, J=1.5 and 9.0 Hz, 1H); 7.41 (partially masked m, 1H); 7.51 (dd, J=8.5 and 11.0 Hz, 1H); from 7.55 to 7.78 (m, 7H); 7.71 (d, J=9.0 Hz, 1H); 8.47 (dd, J=1.5 and 3.0 Hz, 1H); 8.63 (dd, J=2.5 and 7.5 Hz, 1H); 8.98 (spread-out m, 1H); 9.35 (spread-out m, 1H); 10.7 (broad s, 1H); 12.8 (spread-out m, 1H).

MS spectrum (ES⁺): m/z=540 [MH⁺]

EXAMPLE 11

1-(4-{7-Fluoro-3-[(thiophen-3-yl)carbonylamino]-1H-indazol-6-yl}-2-fluorophenyl)-3-(2-fluoro-5-trifluoromethylphenyl)urea

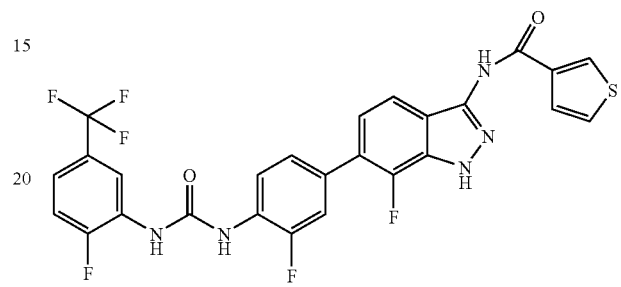

A solution of 0.610 g of (7-fluoro-6-{3-fluoro-4-aminophenyl}-1H-indazol-3-yl)thiophene-3-carboxamide hydrochloride in 30 mL of tetrahydrofuran is admixed with 0.3 g of 2-fluoro-5-trifluoromethylphenyl isocyanate and 0.211 mL of triethylamine. The reaction mixture is stirred for 12 hours at a temperature in the region of 20° C., then concentrated under reduced pressure. Following purification by flash chromatography on a silica column, eluting with a mixture of cyclohexane and ethyl acetate (50/50 by volume), evaporation of the solvents gives 0.287 g of a yellow powder, which is recrystallized from ethyl acetate. This gives 0.154 g of 1-(4-{7-fluoro-3-[(thiophen-3-yl)carbonylamino]-1H-indazol-6-yl}-2-fluorophenyl)-3-(2-fluoro-5-trifluoromethylphenyl)urea in the form of a white solid, whose characteristics are as follows:

¹H NMR spectrum at 300 MHz on a BRUKER AVANCE DPX-300 spectrometer with the chemical shifts (δ in ppm)— in dimethyl sulfoxide-d6 (DMSO-d6) as solvent, referenced at 2.50 ppm:

7.21 (dd, J=6.5 and 8.5 Hz, 1H); 7.41 (m, 1H); 7.50 (t, J=9.0 Hz, 1H); 7.59 (broad d, J=12.0 Hz, 1H ); 7.63 (d, J=8.5 Hz, 1H); 7.69 (dd, J=2.5 and 5.0 Hz, 1H); 7.72 (dd, J=1.5 and 5.0 Hz, 1H); 8.32 (t, J=8.5 Hz, 1H); 8.48 (broad m, 1H); 8.67 (dd, J=2.5 and 7.5 Hz, 1H); 9.34 (spread-out m, 1H); 9.46 (spread-out m, 1H); 10.8 (very spread-out m, 1H); 13.45 (very spread-out m, 1H).

IR spectrum (KBr): 3435; 1706; 1547; 1442; 1341; 1265; 1200; 1127 & 822 cm⁻¹

MS spectrum (ES⁺): m/z=576 [MH⁺]

(7-Fluoro-6-{3-fluoro-4-aminophenyl}-1H-indazol-3-yl)-thiophene-3-carboxamide

A solution of 0.99 g of (7-fluoro-6-{3-fluoro-4-tert-butyloxycarbonylaminophenyl}-1H -indazol-3-yl)thiophene-3-carboxamide in 30 mL of methanol is admixed at ambient temperature with 2.63 mL of a 4N solution of hydrochloric acid in dioxane. The reaction mixture is heated at 40° C. for 4 h and then concentrated to dryness under reduced pressure. The solid obtained is triturated in isopropyl ether and isolated by filtration. Drying under vacuum gives 0.99 g of (7-fluoro- 6-{3-fluoro-4-aminophenyl}-1H-indazol-3-yl)thiophene-3-carboxamide in the form of a yellow solid, whose characteristics are as follows:

MS spectrum (EI): m/z=370 [M⁺]

(7-Fluoro-6-{3-fluoro-4-tert-butyloxycarbonylaminophenyl}-1H-indazol-3-yl)thiophene-3-carboxamide A solution of 1.5 g of tert-butyl [4-(3-amino-7-fluoro-1H-indazol-6-yl)-2-fluoro -phenyl]carbamate in 34 mL of pyridine is admixed at 15° C. with 0.61 g of thiophene-3-carbonyl chloride. The reaction mixture is stirred for 18 h and then poured into distilled water and extracted with ethyl acetate. The organic phase is washed a number of times with distilled water and then with saturated aqueous sodium chloride solution, dried over magnesium sulfate and then concentrated to dryness under reduced pressure. This gives 1.58 g of (7-fluoro-6-{3-fluoro-4-tert-butyloxycarbonylaminophenyl}-1H-indazol-3-yl)thiophene-3-carboxamide in the form of a cream-colored solid, whose characteristics are as follows:

MS spectrum (EI): m/z=470 [M⁺]

tert-Butyl[4-(3-amino-7-fluoro-1H-indazol-6-yl)-2-fluorophenyl]carbamate

A solution of 1.49 g of tert-butyl(4'-cyano-3,2',3'-trifluorobiphenyl-4-yl)carbamate in 40 mL of ethanol is admixed with 2.14 g of hydrazine hydrate and then the mixture is heated at reflux for 18 h. The reaction medium is concentrated to dryness under reduced pressure, the residue is taken up in distilled water and the solid thus obtained is isolated by filtration and then dried. This gives 1.5 g of tert-butyl[4-(3-amino-7-fluoro-1H-indazol-6-yl)-2-fluorophenyl]carbamate in the form of a white solid, whose characteristics are as follows:

MS spectrum (EI): m/z=360 [M⁺]

tert-Butyl(4'-cyano-3,2',3'-trifluorobiphenyl-4-yl)carbamate

A solution of 3.75 g of 4-cyano-2,3-difluorophenyl trifluoromethanesulfonate in 220 mL of dioxane is admixed at ambient temperature with 5 g of N-Boc-4-amino-3-fluorophenylboronic acid, 3.87 g of sodium carbonate in solution with 56 mL of distilled water and then 1.81 g of tetrakistriphenylphosphinepalladium. The reaction mixture is heated for 3 h at reflux and then poured, after cooling, into the distilled water. This mixture is extracted with ethyl acetate, the organic phase is decanted, washed a number of times with distilled water, then with saturated aqueous sodium chloride solution, dried over magnesium sulfate and then concentrated to dryness under reduced pressure. The solid obtained is chromatographed on a silica column (eluent: cyclohexane/ethyl acetate, 90/10 by volume). Evaporation to dryness under reduced pressure of the fractions containing the expected product gives 0.75 g of tert-butyl(4'-cyano-3,2',3'-trifluorobiphenyl-4-yl)carbamate in the form of a pale pink solid, whose characteristics are as follows:

MS spectrum (EI): m/z=348 [M⁺]

4-Cyano-2,3-difluorophenyl trifluoromethanesulfonate

A solution of 5 g of 2,3-difluoro-4-hydroxybenzonitrile in 60 mL of dimethylformamide is admixed at ambient temperature with 1.05 g of 75% sodium hydride and then 12.09 g of N-phenyltrifluoromethanesulfonimide. The reaction mixture is stirred at ambient temperature for 18 h and then poured into distilled water. This mixture is extracted with ethyl acetate and the organic phase is decanted, washed a number of times with distilled water, then with saturated aqueous sodium chloride solution, dried over magnesium sulfate and then concentrated to dryness under reduced pressure. The solid obtained is chromatographed on a silica column (eluent: cyclohexane/ethyl acetate, 80/20 by volume). Evaporation to dryness under reduced pressure of the fractions containing the expected product gives 3.34 g of 4-cyano-2,3-difluorophenyl trifluoromethanesulfonate in the form of a mobile oil, whose characteristics are as follows:

MS spectrum (EI): m/z=287 [M⁺]

EXAMPLE 12

1-(4-{7-Fluoro-3-[(thiophen-3-yl)carbonylamino]-1H-indazol-6-yl}phenyl)-3-phenylurea

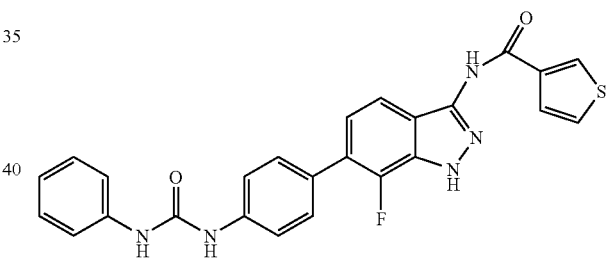

Working in accordance with the procedure described in example 6, 1-(4-{7-fluoro-3-[(thiophen-3-yl)carbonylamino]-1H-indazol-6-yl}phenyl)-3-phenylurea is obtained in the form of a yellow solid, whose characteristics are as follows:

¹H NMR spectrum at 300 MHz on a BRUKER AVANCE DPX-300 spectrometer with the chemical shifts (δ in ppm)—in dimethyl sulfoxide-d6 (DMSO-d6) as solvent, referenced at 2.50 ppm:

6.99 (broad t, J=7.5 Hz, 1H); 7.19 (dd, J=6.5 and 8.5 Hz, 1H); 7.30 (broad t, J=7.5 Hz, 2H); 7.49 (broad d, J=7.5 Hz, 2H); from 7.52 to 7.65 (m, 5H); 7.69 (dd, J=3.0 and 5.0 Hz, 1H); 7.72 (broad d, J=5.0 Hz, 1H); 8.48 (broad m, 1H); 8.83 (broad s, 1H); 8.95 (broad s, 1H); 10.8 (broad s, 1H); 13.35 (broad s, 1H).

IR spectrum (KBr): 3396; 1650; 1597; 1532; 1498; 1234; 742 & 693 cm⁻¹

MS spectrum (ES⁺): m/z=472 [MH⁺]

EXAMPLE 13

1-(4-{7-Fluoro-3-[(thiophen-3-yl)carbonylamino]-1H-indazol-6-yl}phenyl)-3-(5-tert-butylisoxazol-3-yl)urea

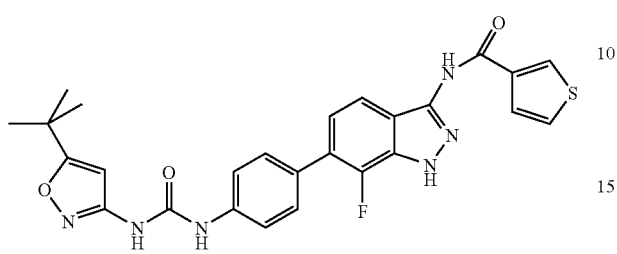

Working in accordance with the procedure described in example 6, 1-(4-{7-fluoro-3-[(thiophen-3-yl)carbonylamino]-1H-indazol-6-yl}phenyl)-3-(5-tert-butylisoxazol-3-yl)urea is obtained in the form of a yellow solid, whose characteristics are as follows:

$^1$H NMR spectrum at 300 MHz on a BRUKER AVANCE DPX-300 spectrometer with the chemical shifts (δ in ppm)—in dimethyl sulfoxide-d6 (DMSO-d6) as solvent, referenced at 2.50 ppm:

1.30 (s, 9H); 6.52 (s, 1H); 7.18 (broad t, J=7.5 Hz, 1H); from 7.52 to 7.64 (m, 5H); 7.68 (dd, J=3.0 and 5.0 Hz, 1H); 7.72 (broad d, J=5.0 Hz, 1H); 8.48 (broad m, 1H); 9.19 (spread-out m, 1H); 9.72 (spread-out m, 1H); 10.8 (broad s, 1H); 13.35 (spread-out m, 1H).

IR spectrum (KBr): 3434; 1607; 1531; 1277; 803 & 741 cm$^{-1}$

MS spectrum (ES$^+$): m/z=519 [MH$^+$]

EXAMPLE 14

1-(4-{7-Fluoro-3-[(thiophen-3-yl)carbonylamino]-1H-indazol-6-yl}phenyl)-3-(2-fluorophenyl)urea

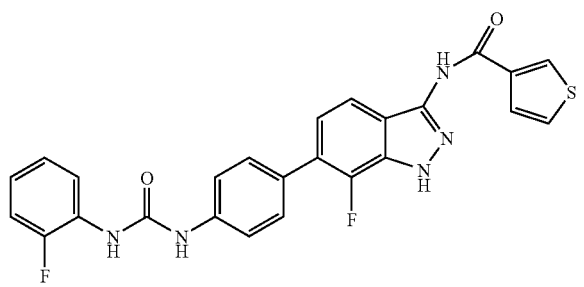

Working in accordance with the procedure described in example 6, 1-(4-{7-fluoro-3-[(thiophen-3-yl)carbonylamino]-1H-indazol-6-yl}phenyl)-3-(2-fluorophenyl)urea is obtained in the form of a yellow solid, whose characteristics are as follows:

$^1$H NMR spectrum at 300 MHz on a BRUKER AVANCE DPX-300 spectrometer with the chemical shifts (δ in ppm)—in dimethyl sulfoxide-d6 (DMSO-d6) as solvent, referenced at 2.50 ppm:

7.02 (m, 1H); from 7.10 to 7.30 (m, 3H); from 7.52 to 7.65 (m, 5H); 7.68 (dd, J=3.0 and 5.0 Hz, 1H); 7.72 (broad d, J=5.0 Hz, 1H); 8.18 (dt, J=2.0 and 8.5 Hz, 1H); 8.47 (broad m, 1H); 8.65 (broad m, 1H); 9.30 (broad s, 1H); 10.8 (spread-out m, 1H); 13.35 (spread-out m, 1H).

IR spectrum (KBr): 3267; 1650; 1598; 1532; 1455; 1249; 1184 & 746 cm$^{-1}$

MS spectrum (ES$^+$): m/z=490 [MH$^+$]

EXAMPLE 15

1-(4-{7-Fluoro-3-[(thiophen-3-yl)carbonylamino]-1H-indazol-6-yl}phenyl)-3-(5-trifluoromethylphenyl)urea

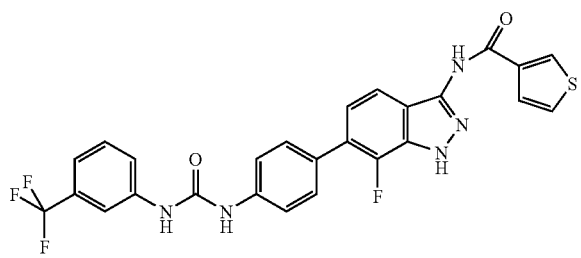

Working in accordance with the procedure described in example 6, 1-(4-{7-fluoro-3-[(thiophen-3-yl)carbonylamino]-1H-indazol-6-yl}phenyl)-3-(5-trifluoromethylphenyl)urea is obtained in the form of a white solid, whose characteristics are as follows:

$^1$H NMR spectrum at 300 MHz on a BRUKER AVANCE DPX-300 spectrometer with the chemical shifts (δ in ppm)—in dimethyl sulfoxide-d6 (DMSO-d6) as solvent, referenced at 2.50 ppm:

7.19 (dd, J=6.5 and 8.5 Hz, 1H); 7.31 (broad d, J=7.5 Hz, 1H); 7.52 (t, J=7.5 Hz, 1H); from 7.55 to 7.68 (m, 6H); 7.68 (dd, J=3.0 and 5.0 Hz, 1H); 7.72 (dd, J=1.5 and 5.0 Hz, 1H); 8.04 (broad s, 1H); 8.48 (dd, J=1.5 and 3.0 Hz, 1H); 9.28 (broad s, 1H); 9.42 (broad s, 1H); 10.8 (broad s, 1H); 13.35 (broad s, 1H).

IR spectrum (KBr): 3334; 1691; 1644; 1534; 1341; 1114; 807 & 699 cm$^{-1}$

MS spectrum (ES$^+$): m/z=540 [MH$^+$]

EXAMPLE 16

1-(4-{7-Fluoro-3-[(thiophen-3-yl)carbonylamino]-1H-indazol-6-yl}phenyl)-3-(5-tert-butyl-2-p-tolyl-2H-pyrazol-3-yl)urea

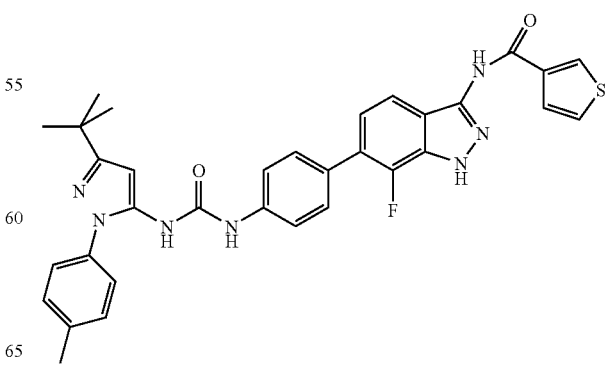

Working in accordance with the procedure described in example 6, 1-(4-{7-fluoro-3-[(thiophen-3-yl)carbonylamino]-1H-indazol-6-yl}phenyl)-3-(5-tert-butyl-2-p-tolyl-2H-pyrazol-3-yl)urea is obtained in the form of a yellow solid, whose characteristics are as follows:

Melting point: 196-197° C.

$^1$H NMR spectrum at 300 MHz on a BRUKER AVANCE DPX-300 spectrometer with the chemical shifts (δ in ppm)— in dimethyl sulfoxide-d6 (DMSO-d6) as solvent, referenced at 2.50 ppm:

1.29 (s, 9H); 2.39 (s, 3H); 6.37 (s, 1H); 7.16 (m, 1H); 7.32 (broad d, J=8.5 Hz, 2H); 7.42 (broad d, J=8.5 Hz, 2H); 7.56 (broad s, 4H); 7.61 (d, J=8.5 Hz, 1H); 7.68 (broad m, 1H); 7.72 (dd, J=1.5 and 5.0 Hz, 1H); 8.47 (broad m, 1H); 8.67 (spread-out m, 1H 9.42 (spread-out m, 1H); 10.75 (broad s, 1H); 13.45 (spread-out m, 1H).

IR spectrum (KBr): 3435; 1646; 1533; 1410; 1202; 823 & 741 cm$^{-1}$

MS spectrum (ES$^+$): m/z=608 [MH$^+$]

EXAMPLE 17

1-(4-{7-Fluoro-3-[(furan-2-yl)carbonylamino]-1H-indazol-6-yl}phenyl)-3-(2-fluoro-5-trifluoromethylphenyl)urea

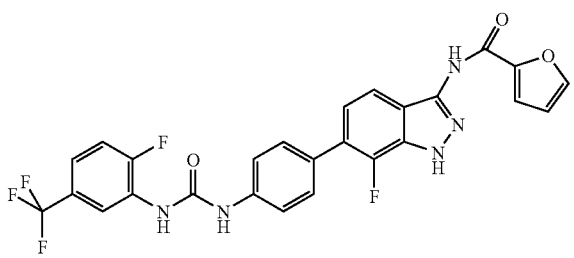

A solution of 223.7 mg of 1-[4-(3-amino-7-fluoro-1H-indazol-6-yl)phenyl]-3-(2-fluoro-5-trifluoromethylphenyl)urea (obtained in accordance with the procedure described in example 7) in 5 mL of pyridine is admixed at ambient temperature with 65.3 mg of 2-furoyl chloride. The reaction mixture is stirred at ambient temperature for 48 h and then poured into distilled water. This mixture is extracted with ethyl acetate and the organic phase is decanted, washed a number of times with distilled water, then with saturated aqueous sodium chloride solution, dried over magnesium sulfate then concentrated to dryness under reduced pressure. The solid obtained is chromatographed on a silica column (eluent: cyclohexane/ethyl acetate, 50/50 by volume). Evaporation to dryness under reduced pressure of the fractions containing the expected product gives 72 mg of a white solid, which is purified again by LCMS. This gives 22.7 mg of 1-(4-{7-fluoro-3-[(furan-2-yl)carbonylamino]-1H-indazol-6-yl}phenyl)-3-(2-fluoro-5-trifluoromethylphenyl)urea in the form of a pale yellow solid, whose characteristics are as follows:

Melting point: 152-153° C.

$^1$H NMR spectrum at 400 MHz on a BRUKER AVANCE DRX-400 spectrometer with the chemical shifts (δ in ppm)— in dimethyl sulfoxide-d6 (DMSO-d6) as solvent, referenced at 2.50 ppm:

6.72 (dd, J=2.0 and 3.5 Hz, 1H); 7.19 (dd, J=6.5 and 8.5 Hz, 1H); 7.40 (m, 1H); from 7.47 to 7.54 (m, 2H); from 7.58 to 7.65 (m, 5H); 7.98 (broad m, 1H); 8.62 (dd, J=2.5 and 7.5 Hz, 1H); 9.02 (broad d, J=2.0 Hz, 1H); 9.41 (broad s, 1H); 10.85 (broad s, 1H); 13.4 (broad s, 1H).

IR spectrum (KBr): 3435; 1669; 1603; 1545; 1442; 1341; 1122; 711 & 614 cm$^{-1}$ MS spectrum (EI): m/z=541 [M$^{+\circ}$]

EXAMPLE 18

1-(4-{7-Fluoro-3-[phenylcarbonylamino]-1H-indazol-6-yl}phenyl)-3-(2-fluoro-5-trifluoromethylphenyl)urea

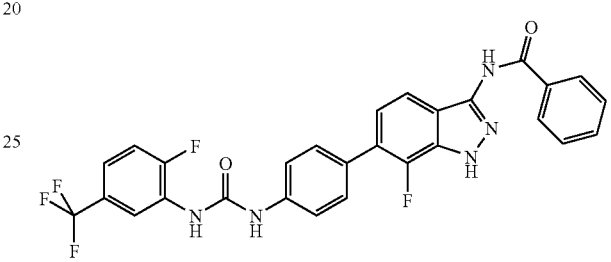

A solution of 223.7 mg of 1-[4-(3-amino-7-fluoro-1H-indazol-6-yl)phenyl]-3-(2-fluoro-5-trifluoromethylphenyl)urea (obtained in accordance with the procedure described in example 7) in 5 mL of pyridine is admixed at ambient temperature with 70 mg of benzoyl chloride. The reaction mixture is stirred at ambient temperature for 48 h and then poured into distilled water. This mixture is extracted with ethyl acetate and the organic phase is decanted, washed a number of times with distilled water, then with saturated aqueous sodium chloride solution, dried over magnesium sulfate then concentrated to dryness under reduced pressure. The solid obtained is chromatographed on a silica column (eluent: cyclohexane/ethyl acetate, 50/50 by volume). Evaporation to dryness under reduced pressure of the fractions containing the expected product gives 115 mg of a beige-gray solid, which is purified again by LCMS.

This gives 46 mg of 1-(4-{7-fluoro-3-[phenylcarbonylamino]-1H-indazol-6-yl}phenyl)-3-(2-fluoro-5-trifluoromethylphenyl)urea in the form of a pale yellow solid, whose characteristics are as follows:

Melting point: 206-207° C.

$^1$H NMR spectrum at 400 MHz on a BRUKER AVANCE DRX-400 spectrometer with the chemical shifts (δ in ppm)— in dimethyl sulfoxide-d6 (DMSO-d6) as solvent, referenced at 2.50 ppm:

7.19 (broad t, J=7.5 Hz, 1H); 7.40 (m, 1H); de 7.47 at 7.67 (m, 9H); 8.09 (broad d, J=8.5 Hz, 2H); 8.62 (dd, J=2.0 and 7.5 Hz, 1H); 9.19 (broad s, 1H); 9.60 (broad s, 1H); 10.9 (broad s, 1H); 13.4 (spread-out m, 1H).

IR spectrum (KBr): 3419; 1669; 1599; 1552; 1443; 1342; 1190; 1118; 804; 760 & 614 cm$^{-1}$ MS spectrum (EI): m/z=551 [M$^{+\circ}$]

EXAMPLE 19

1-[4-(3-Amino-7-fluoro-1H-indazol-6-yl)phenyl]-3-(3-trifluoromethylphenyl)urea

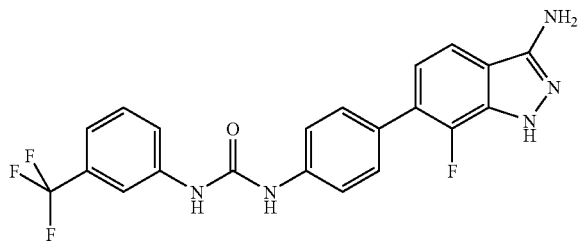

A solution of 150 mg of 6-(4-aminophenyl)-7-fluoro-1H-indazol-3-ylamine in 7 mL of anhydrous tetrahydrofuran is admixed at ambient temperature with 128.7 mg of 3-trifluoromethylphenyl isocyanate. The reaction mixture is stirred at ambient temperature for 18 h and then concentrated to dryness under reduced pressure. The solid obtained is purified by LCMS. This gives 84 mg of 1-[4-(3-amino-7-fluoro-1H-indazol-6-yl)phenyl]-3-(3-trifluoromethylphenyl)urea in the form of a white solid, whose characteristics are as follows:

$^1$H NMR spectrum at 300 MHz on a BRUKER AVANCE DRX-300 spectrometer, with the chemical shifts (δ in ppm)—in dimethyl sulfoxide-d6 (DMSO-d6) as solvent, referenced at 2.50 ppm:

5.47 (broad s, 2H); 6.99 (dd, J=6.5 and 8.5 Hz, 1H); 7.30 (broad d, J=7.5 Hz, 1H); from 7.47 to 7.69 (m, 7H); 8.04 (broad s, 1H); 9.60 (spread-out m, 1H); 9.78 (spread-out m, 1H); 11.85 (broad s, 1H).

IR spectrum (KBr): 3403; 1658; 1605; 1533; 1448; 1338; 1125; 798 & 698 cm$^{-1}$ MS spectrum (ES$^+$): m/z=430 [MH$^+$]

6-(4-Aminophenyl)-7-fluoro-1H-indazol-3-ylamine

A suspension of 3 g of tert-butyl[4-(3-amino-7-fluoro-1H-indazol-6-yl)phenyl]carbamate in 60 mL of dichloromethane is admixed at ambient temperature with 6 mL of trifluoroacetic acid. The reaction mixture is stirred at ambient temperature for 18 h and concentrated to dryness under reduced pressure. The solid obtained is taken up in ethyl acetate and the solution is treated with 4N aqueous sodium hydroxide solution and then decanted. The organic phase is subsequently washed with distilled water, then with saturated aqueous sodium chloride solution, dried over magnesium sulfate, filtered and then concentrated to dryness under reduced pressure. The yellow solid obtained (2.08 g) is chromatographed on a silica column (eluent: ethyl acetate). Evaporation to dryness under reduced pressure of the fractions containing the expected product gives 1.88 g of 6-(4-aminophenyl)-7-fluoro-1H-indazol-3-ylamine in the form of a yellow solid, whose characteristics are as follows:

MS spectrum (EI): m/z=242 [M$^+$]

tert-Butyl[4-(3-amino-7-fluoro-1H-indazol-6-yl)phenyl]carbamate

A suspension of 7.89 g of tert-butyl(4'-cyano-2',3'-difluorobiphenyl-4-yl)carbamate in 50 mL of isopropanol is heated to 50° C. and then admixed at that temperature with 5.8 mL of hydrazine hydrate. The reaction mixture is stirred at reflux for 18 h and then poured, after cooling, into 500 mL of distilled water. The white precipitate formed is isolated by filtration and dried under vacuum at 50° C. This gives 8.39 g of tert-butyl[4-(3-amino-7-fluoro-1H-indazol-6-yl)phenyl]carbamate in the form of a yellow solid, whose characteristics are as follows:

MS spectrum (ES): m/z=343 [MH$^+$]

tert-Butyl(4'-cyano-2',3'-difluorobiphenyl-4-yl)carbamate

A solution of 7 g of 4-cyano-2,3-difluorophenyl trifluoromethanesulfonate in 400 mL of dioxane is admixed at ambient temperature with 8.67 g of N-Boc 4-amino-3-fluorophenylboronic acid, 7.235 g of sodium carbonate in solution in 100 mL of distilled water, and then 3.38 g of tetrakistriphenylphosphinepalladium. The reaction mixture is heated at 90° C. for 3 h and then concentrated to dryness under reduced pressure. The solid obtained is taken up in ethyl acetate; this organic phase is washed a number of times with distilled water and then with saturated sodium chloride solution, dried over magnesium sulfate and then concentrated to dryness under reduced pressure. The solid obtained is chromatographed on a silica column (eluent: cyclohexane/ethyl acetate, 90/10 by volume). Evaporation to dryness under reduced pressure of the fractions containing the expected product gives 7.89 g of tert-butyl(4'-cyano-3,2',3'-trifluorobiphenyl-4-yl)carbamate in the form of a cream-white solid, whose characteristics are as follows:

MS spectrum (EI): m/z=330 [M$^+$]

EXAMPLE 20

1-[4-(3-Amino-7-fluoro-1H-indazol-6-yl)phenyl]-3-phenylurea

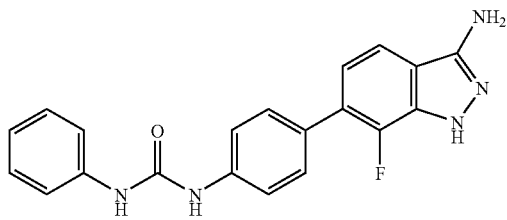

Working in accordance with the procedure described in example 19, 1-[4-(3-amino-7-fluoro-1H-indazol-6-yl)phenyl]-3-phenylurea is obtained in the form of a white solid, whose characteristics are as follows:

$^1$H NMR spectrum at 300 MHz on a BRUKER AVANCE DRX-300 spectrometer with the chemical shifts (δ in ppm)—in dimethyl sulfoxide-d6 (DMSO-d6) as solvent, referenced at 2.50 ppm:

5.46 (broad s, 2H); 6.98 (m, 2H); 7.29 (broad t, J=8.0 Hz, 2H); from 7.45 to 7.61 (m, 7H); 8.93 (spread-out m, 1H); 9.03 (spread-out m, 1H); 11.85 (broad s, 1H).

IR spectrum (KBr): 3415; 1646; 1598; 1532; 1443; 1316; 1234; 752 & 693 cm$^{-1}$ MS spectrum (EI): m/z=361 [M$^{+\circ}$]

EXAMPLE 21

1-[4-(3-Amino-7-fluoro-1H-indazol-6-yl)phenyl]-3-(5-tert-butylisoxazol-3-yl)urea

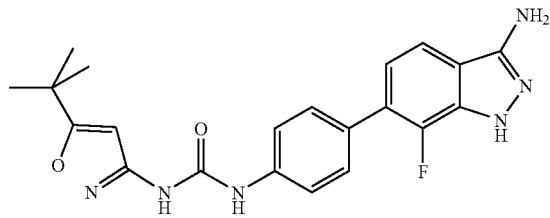

Working in accordance with the procedure described in example 19, 1-[4-(3-amino-7-fluoro-1H-indazol-6-yl)phenyl]-3-(5-tert-butylisoxazol-3-yl)urea is obtained in the form of a white solid, whose characteristics are as follows:

$^1$H NMR spectrum at 300 MHz on a BRUKER AVANCE DRX-300 spectrometer with the chemical shifts (δ in ppm)—in dimethyl sulfoxide-d6 (DMSO-d6) as solvent, referenced at 2.50 ppm:

1.30 (s, 9H); 5.47 (broad s, 2H); 6.52 (s, 1H); 6.98 (dd, J=6.5 and 8.5 Hz, 1H); from 7.50 to 7.61 (m, 5H); 9.22 (spread-out m, 1H); 9.79 (spread-out m, 1H); 11.85 (broad s, 1H).

IR spectrum (KBr): 3414; 1696; 1607; 1530; 1431; 1317; 1202; 912 & 800 cm$^{-1}$ MS spectrum (EI): m/z=408 [M$^{+o}$]

EXAMPLE 22

1-[4-(3-Amino-7-fluoro-1H-indazol-6-yl)phenyl]-3-(2-fluorophenyl)urea

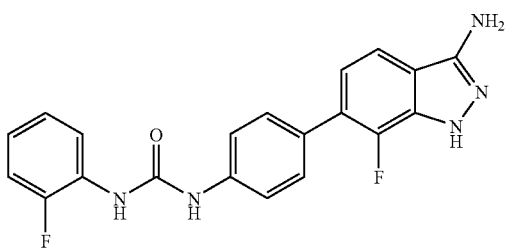

Working in accordance with the procedure described in example 19, 1-[4-(3-amino-7-fluoro-1H-indazol-6-yl)phenyl]-3-(2-fluorophenyl)urea is obtained in the form of a white solid, whose characteristics are as follows:

$^1$H NMR spectrum at 300 MHz on a BRUKER AVANCE DRX-300 spectrometer with the chemical shifts (δ in ppm)—in dimethyl sulfoxide-d6 (DMSO-d6) as solvent, referenced at 2.50 ppm:

5.47 (broad s, 2H); 6.98 (dd, J=6.5 and 8.5 Hz, 1H); 7.03 (m, 1H); 7.15 (broad t, J=8.5 Hz, 1H); 7.24 (ddd, J=2.0-8.5 and 12.0 Hz, 1H); from 7.50 to 7.61 (m, 5H); 8.16 (dt, J=2.0 and 8.5 Hz, 1H); 8.65 (spread-out m, 1H); 9.27 (broad s, 1H); 11.85 (broad s, 1H)

IR spectrum (KBr): 3347; 1655; 1603; 1533; 1457; 1251; 1193; 797 & 752 cm$^{-1}$ MS spectrum (EI): m/z=379 [M$^{+o}$]

EXAMPLE 23

1-(4-{7-Fluoro-3-[(thiophen-3-yl)carbonylamino]-1H-indazol-6-yl}-2-methylphenyl)-3-(2-fluoro-5-trifluoromethylphenyl)urea

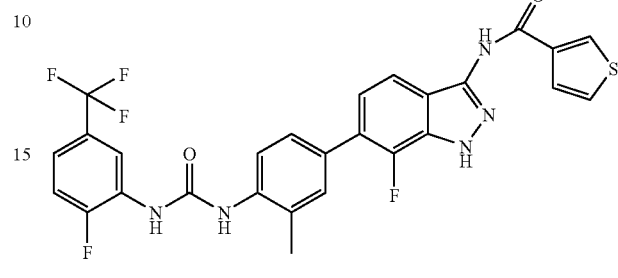

Working in accordance with the procedure described in example 11, 1-(4-{7-fluoro-3-[(thiophen-3-yl)carbonylamino]-1H-indazol-6-yl}-2-methylphenyl)-3-(2-fluoro-5-trifluoromethylphenyl)urea is obtained in the form of a pale yellow solid, whose characteristics are as follows:

Melting point: 312-313° C.

$^1$H NMR spectrum at 400 MHz on a BRUKER AVANCE DRX-400 spectrometer with the chemical shifts (δ in ppm)—in dimethyl sulfoxide-d6 (DMSO-d6) as solvent, referenced at 2.50 ppm:

2.37 (s, 3H); 7.18 (dd, J=6.5 and 8.5 Hz, 1H); 7.39 (m, 1H); from 7.43 to 7.54 (m, 3H); 7.62 (d, J=8.5 Hz, 1H); 8.68 (dd, J=3.0 and 5.0 Hz, 1H); 7.72 (dd, J=1.5 and 5.0 Hz, 1H); 8.03 (d, J=8.5 Hz, 1H); 8.47 (broad m, 1H); 8.62 (s, 1H); 8.69 (dd, J=2.5 and 7.5 Hz, 1H); 9.41 (broad s, 1H); 10.8 (broad s, 1H); 13.4 (spread-out m, 1H).

IR spectrum (KBr): 3301; 1660; 1542; 1442; 1339; 1263; 1126; 819; 742 & 619 cm$^{-1}$ MS spectrum (CI): m/z=572 [MH$^+$]

EXAMPLE 24

1-(5-{7-Fluoro-3-[(thiophen-3-yl)carbonylamino]-1H-indazol-6-yl}pyridin-2-yl)-3-(2-fluoro-5-trifluoromethylphenyl)urea

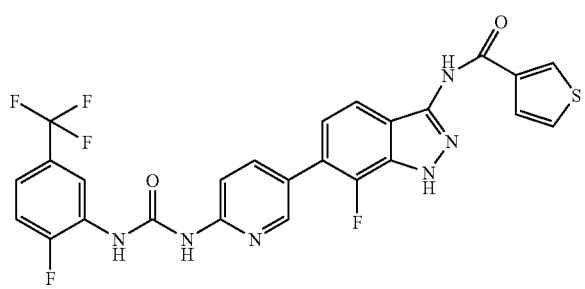

Working in accordance with the procedure described in example 11, 1-(5-{7-fluoro-3-[(thiophen-3-yl)carbonylamino]-1H-indazol-6-yl}pyridin-2-yl)-3-(2-fluoro-5-trifluoromethylphenyl)urea is obtained in the form of a solid, whose characteristics are as follows:

<sup>1</sup>H NMR spectrum at 400 MHz on a BRUKER AVANCE DRX-400 spectrometer with the chemical shifts (δ in ppm)—in dimethyl sulfoxide-d6 (DMSO-d6) as solvent, referenced at 2.50 ppm:

7.24 (dd, J=6.5 and 8.5 Hz, 1H); 7.45 (m, 1H); 7.55 (dd, J=8.5 and 11.0 Hz, 1H); from 7.63 to 7.70 (m, 3H); 7.73 (dd, J=1.5 and 5.0 Hz, 1H); 8.11 (dm, J=8.5 Hz, 1H); 8.47 (m, 1H); 8.58 (m, 1H); 8.69 (dd, J=2.5 and 7.5Hz, 1H); 10.1 (s, 1H); 10.8 (s, 1H); 11.6 (broad s, 1H); 13.5 (spread-out m, 1H).

MS spectrum (ES$^+$): m/z=559 [MH$^+$]

EXAMPLE 25

1-[4-(3-Amino-7-fluoro-1H-indazol-6-yl)phenyl]-3-(5-tert-butyl-2-p-tolyl-2H-pyrazol-3-yl)urea

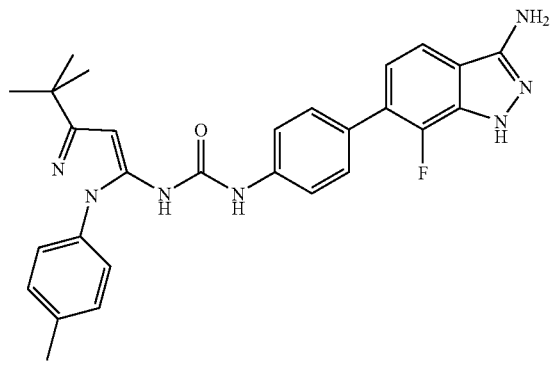

Working in accordance with the procedure described in example 19, 1-[4-(3-amino-7-fluoro-1H-indazol-6-yl)phenyl]-3-(5-tert-butyl-2-p-tolyl-2H-pyrazol-3-yl)urea is obtained in the form of a white solid, whose characteristics are as follows:

<sup>1</sup>H NMR spectrum at 400 MHz on a BRUKER AVANCE DRX-400 spectrometer with the chemical shifts (δ in ppm)—in dimethyl sulfoxide-d6 (DMSO-d6) as solvent, referenced at 2.50 ppm:

1.29 (s, 9H); 2.38 (s, 3H); 5.48 (broad s, 2H); 6.38 (s, 1H); 6.97 (m, 1H); 7.34 (broad d, J=8.5 Hz, 2H); 7.41 (broad d, J=8.5 Hz, 2H); from 7.48 to 7.57 (m, 5H); 8.40 (broad s, 1H); 9.17 (broad s, 1H); 11.85 (spread-out m, 1H).

MS spectrum (ES$^+$): m/z=498 [MH$^+$]

EXAMPLE 26

1-(4-{7-Fluoro-3-[(L-pyrrolidin-2-yl)carbonylamino]-1H-indazol-6-yl}phenyl)-3-(2-fluoro-5-trifluoromethylphenyl)urea

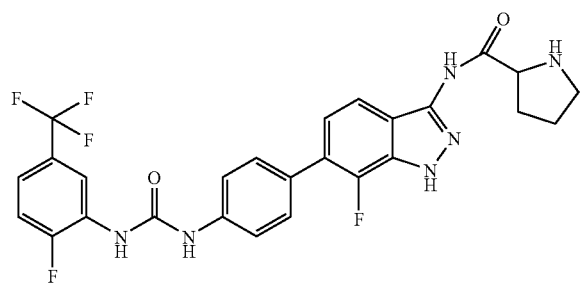

A solution of 0.23 g of 1-(4-{7-fluoro-3-[(N-Boc-L-pyrrolidin-2-yl)carbonylamino]-1H -indazol-6-yl}phenyl)-3-(2-fluoro-5-trifluoromethylphenyl)urea in 20 mL of dioxane is admixed at ambient temperature with 1 mL of a 4N aqueous solution of hydrochloric acid. The reaction mixtures is stirred at 50° C. for 3 h and then concentrated to dryness under reduced pressure. The solid obtained is taken up in dichloromethane and the precipitate is isolated by filtration. The solid obtained (96 mg) is purified by LCMS. This gives 16 mg of 1-(4-{7-fluoro-3-[(L-pyrrolidin-2-yl)carbonylamino]-1H-indazol-6-yl}phenyl)-3-(2-fluoro-5-trifluoromethylphenyl)urea in the form of a beige solid, whose characteristics are as follows:

IR spectrum (KBr): 3271; 1703; 1625; 1538; 1442; 1341; 1257; 1198; 1117 & 807 cm$^{-1}$ MS spectrum (EI): m/z=544 [M$^{+o}$]

1-(4-{7-Fluoro-3-[(N-Boc-L-pyrrolidin-2-yl)carbonylamino]-1H-indazol-6-yl}-phenyl)-3-(2-fluoro-5-trifluoromethylphenyl)urea Working in accordance with the procedure described in example 17, 1-(4-{7-fluoro-3-[(N-Boc-L-pyrrolidin-2-yl)carbonylamino]-1H-indazol-6-yl}phenyl)-3-(2-fluoro-5-trifluoromethylphenyl)urea is obtained in the form of a bright yellow solid, whose characteristics are as follows:

MS spectrum (ES): m/z=645 [MH$^+$]

EXAMPLE 27

1-(4-{7-Fluoro-3-acetylamino-1H-indazol-6-yl}phenyl)-3-(2-fluoro-5-trifluoromethylphenyl)urea

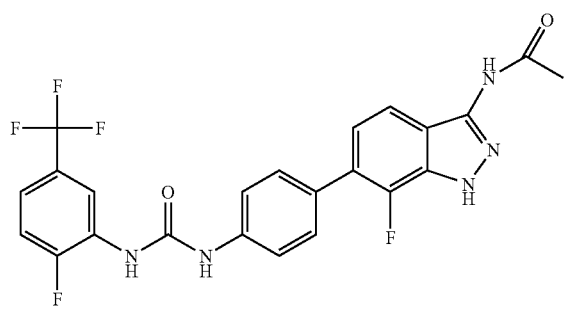

Working in accordance with the procedure described in example 17, 1-(4-{7-fluoro-3-acetylamino-1H-indazol-6-yl}phenyl)-3-(2-fluoro-5-trifluoromethylphenyl)urea is obtained in the form of a bright yellow solid, whose characteristics are as follows:

<sup>1</sup>H NMR spectrum at 400 MHz on a BRUKER AVANCE DRX-400 spectrometer with the chemical shifts (δ in ppm)—in dimethyl sulfoxide-d6 (DMSO-d6) as solvent, referenced at 2.50 ppm:

2.11 (s, 3H); 7.14 (m, 1H); 7.40 (m, 1H); 7.50 (dd, J=8.5 and 11.0 Hz, 1H); from 7.55 to 7.64 (m, 4H); 7.67 (d, J=8.5 Hz, 1H); 8.62 (dd, J=2.5 and 7.5 Hz, 1H); 9.11 (broad s, 1H); 9.50 (broad s, 1H); 10.5 (broad s, 1H); 13.2 (broad s, 1H).

IR spectrum (KBr): 3422; 1710; 1670; 1604; 1550; 1442; 1341; 1125; 818 & 614 cm$^{-1}$ MS spectrum (ES$^+$): m/z=490 [MH$^+$]

EXAMPLE 28

1-(4-(7-Fluoro-3-formylamino-1H-indazol-6-yl}phenyl)-3-(2-fluoro-5-tri-fluoromethylphenyl)urea

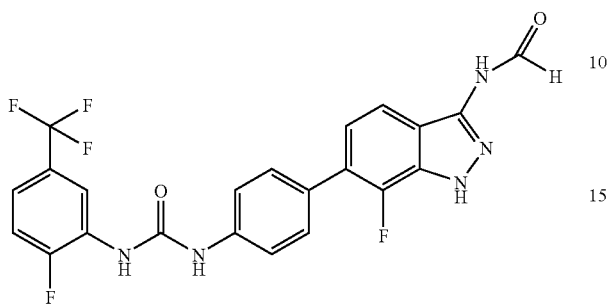

A solution of 0.633 mL of acetic anhydride and 0.253 mL of formic acid is heated at 50° C. for 2 h and then admixed dropwise with a solution of 300 mg of 1-[4-(3-amino-7-fluoro-1H-indazol-6-yl)phenyl]-3-(2-fluoro-5-trifluoromethylphenyl)urea (obtained in accordance with the procedure described in example 7) in 7 mL of pyridine. The reaction mixture is stirred at ambient temperature for 24 h and then poured into distilled water. This mixture is filtered and then the solid obtained (256 mg) is purified by LCMS. This gives 34 mg of 1-(4-{7-fluoro-3-formylamino-1H-indazol-6-yl}phenyl)-3-(2-fluoro-5-trifluoromethylphenyl)urea in the form of a beige solid, whose characteristics are as follows:

$^1$H NMR spectrum at 300 MHz on a BRUKER AVANCE DPX-300 spectrometer with the chemical shifts (δ in ppm)— in dimethyl sulfoxide-d6 (DMSO-d6) as solvent, referenced at 2.50 ppm following addition of one drop of acetic acid -d4 (CD3COOD):

A 60%-40% mixture is observed of the two imino alcohol forms of the expected product:

7.19 (m, 1H); 7.40 (m, 1H); 7.51 (m, 1H); from 7.55 to 7.65 (m, 4H); 7.69 (d, J=8.5 Hz, 0.6H); 7.77 (d, J=8.5 Hz, 0.4H); 8.32 (s, 0.4H); 8.65 (dd, J=2.5 and 7.5 Hz, 1H); 8.98 (s, 0.6H).

IR spectrum (KBr): 3372; 3308; 1680; 1604; 1551; 1443; 1341; 1263; 1118; 812 & 614 cm$^{-1}$ MS spectrum (EI): m/z=475 [M$^{+o}$]

EXAMPLE 29

N-[6-(4-Aminophenyl)-7-fluoro-1H-indazol-3-yl]thiophene-3-carboxamide

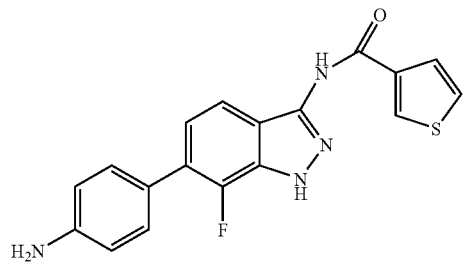

A solution of 1.46 g of 6-(4-tert-butoxycarbonylaminophenyl)-1-[3-(thiophen-3-yl)carbonylamino]-7-fluoro-1H-indazole in 20 mL of dichloromethane is admixed with 10 mL of trifluoroacetic acid and 1 mL of water. The reaction mixture is stirred for 16 hours at a temperature in the region of 20° C. and then is concentrated under reduced pressure. The solid residue is taken up in ethyl acetate and washed with saturated sodium bicarbonate solution until an aqueous phase with a pH of 9 is obtained, at which point it is washed with water. The organic phase is concentrated under reduced pressure, to give 1.02 g of N-[6-(4-aminophenyl)-7-fluoro-1H-indazol-3-yl]thiophene-3-carboxamide, with a yield by weight of 91%.

The characteristics are as follows:

LCMS analysis: [M+H]+=353.2; retention time: 2.92 min

The synthesis of 6-(4-tert-butoxycarbonylaminophenyl)-1-[3-(thiophen-3-yl)-carbonylamino]-7-fluoro-1H-indazole is described in example 4.

EXAMPLES 30 TO 39

A solution of 100 mg (0.284 mmol) of N-[6-(4-aminophenyl)-7-fluoro-1H-indazol-3-yl]thiophene-3-carboxamide in 4.5 mL of pyridine is admixed at 0° C. with solutions of 0.284 mmol of sulfonyl chlorides in 1 mL of dichloromethane. The reaction mixtures are stirred for 72 hours at a temperature in the region of 20° C. and then concentrated under reduced pressure. The dry residues are taken Lip in methanol and concentrated under reduced pressure. The dry residues are taken up in 1.5 mL of a methanol/acetic acid/dimethyl sulfoxide mixture and purified by preparative LC/MS.

The NMR analyses are conducted as follows: $^1$H NMR spectrum at 400 MHz on a BRUKER AVANCE DRX-400 spectrometer, with the chemical shifts (δ in ppm)—in dimethyl sulfoxide-d6 (DMSO-d6) as solvent, referenced at 2.50 ppm:

The products are described in the following table:

| Example N° | Structure | Name | Sulfonyl chloride precursor | Amount Yield | Analyses |
|---|---|---|---|---|---|
| 30 | 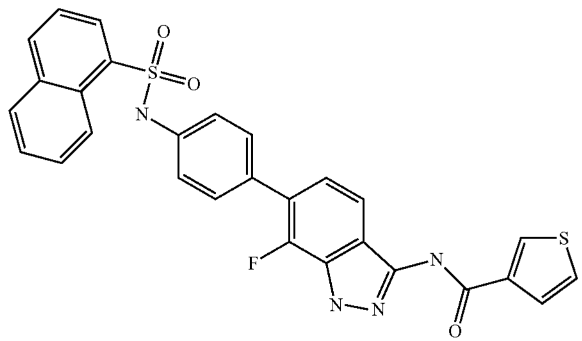 | Thiophene-3-carboxylic acid {7-fluoro-6-[4-(naphthalene-1-sulfonylamino)phenyl]-1H-indazol-3-yl}-amide | | 99 mg 64% | IR spectrum: KBr 3404; 1659; 1530; 1338; 1161; 1134 &769 cm$^{-1}$ NMR: 7.03 (dd, J = 7.0 and 8.5 Hz, 1H); 7.17 (broad d, J = 9.0 Hz, 2H); 7.45 (broad d, J = 9.0 Hz, 2H); 7.55 (d, J = 8.5 Hz, 1H); from 7.63 to 7.71 (m, 4H); 7.76 (broad t, J = 8.0 Hz, 1H); 8.09 (broad d, J = 8.0 Hz, 1H); 8.24 (broad d, J = 8.0 Hz, 1H); 8.30 (broad d, J = 8.0 Hz, 1H); 8.45 (broad d, J = 2.5 Hz, 1H); 8.76 (broad d, J = 8.5 Hz, 1H); 10.75 (s, 1H); 10.9 (broad s,1H); 13.3 (s, 1H). |
| 31 | 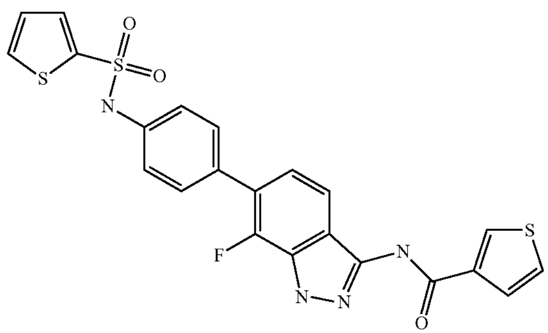 | Thiophene-3-carboxylic acid {7-fluoro-6-[4-(thiophene-2-sulfonylamino)phenyl]-1H-indazol-3-yl}-amide | | 113 mg 80% | IR spectrum: KBr 3425; 1650; 1528; 1340; 1159; 729 &593 cm$^{-1}$ NMR: from 7.10 to 7.16 (m, 2H); 7.28 (broad d, J = 9.0 Hz, 2H); 7.57(broad d, J = 8.5 Hz, 2H); from 7.59 to 7.64 (m, 2H); 7.67 (dd, J = 3.0 and 5.0 Hz, 1H); 7.71 (broad d, J = 5.0 Hz, 1H); 7.93 (broad d, J = 5.5 Hz, 1H); 8.47 (broad d, J = 2.5 Hz, 1H); 10.65 (broad s, 1H); 10.8 (s, 1H); 13.4 (s, 1H). |

| Example N° | Structure | Name | Sulfonyl chloride precursor | Amount Yield | Analyses |
|---|---|---|---|---|---|
| 32 | 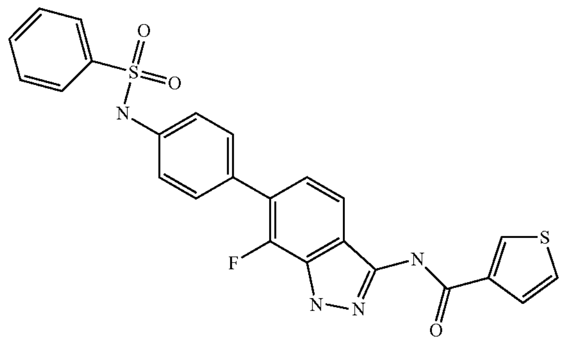 | Thiophene-3-carboxylic acid [6-(4-benzenesulfonylaminophenyl)-7-fluoro-1H-indazol-3-yl]-amide | | 121 mg 87% | IR spectrum: KBr 3360; 3174; 1652; 1541; 1529; 1341, 1159, 913, 687 &580 cm$^{-1}$ NMR: 7.10 (dd, J = 7.0 and 8.5 Hz, 1H); 7.24 (broad d, J = 9.0 Hz, 2H); 7.52 (broad d, J = 9.0 Hz, 2H); from 7.56 to 7.65 (m, 4H); 7.67 (dd, J = 3.0 and 5.0 Hz, 1H); 7.71 (broad d, J = 5.0 Hz, 1H); 8.84 (broad d, J = 8.5 Hz, 2H); 8.46 (broad d, J = 2.5 Hz, 1H); 10.5 (s, 1H); 10.8 (broad s, 1H); 13.35 (broad s, 1H). |
| 33 | 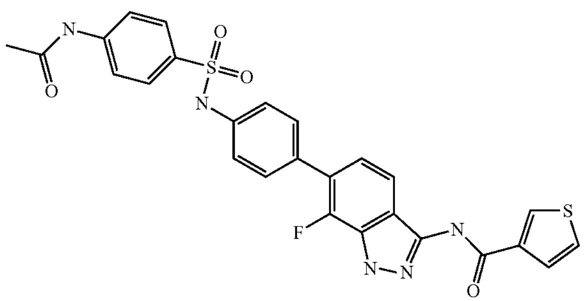 | Thiophene-3-carboxylic acid {6-[4-(4-acetylaminobenzenesulfonylamino)phenyl]-7-fluoro-1H-indazol-3-yl}-amide | | 19 mg 12% | LC/MS [M + H]+ = 550.2 retention time: 3.58 min |
| 34 | 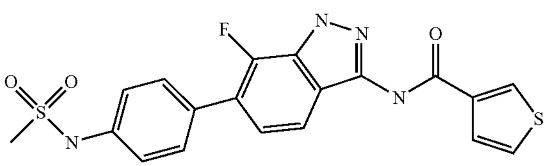 | Thiophene-3-carboxylic acid [7-fluoro-6-(4-methanesulfonylaminophenyl)-1H-indazol-3-yl]-amide | | 82 mg 67% | IR spectrum: KBr 3362; 1646; 1529; 1332; 1149; 971; 542 &507 cm$^{-1}$ NMR: 3.06 (s, 3H); 7.16 (dd, J = 7.0 and 8.5 Hz, 1H); 7.34 (broad d, J = 9.0 Hz, 2H); 7.63 (broad d, J = 9.0 Hz, 3H); 7.68 (dd, J = 3.0 and 5.0 Hz, 1H); 7.72 (broad d, J = 5.0 Hz, 1H); 8.47 (broad d, J = 2.5 Hz, 1H); 9.93 (broad s, 1H); 10.8 (s, 1H); 13.4 (broad s, 1H). |

| Example N° | Structure | Name | Sulfonyl chloride precursor | Amount Yield | Analyses |
|---|---|---|---|---|---|
| 35 | 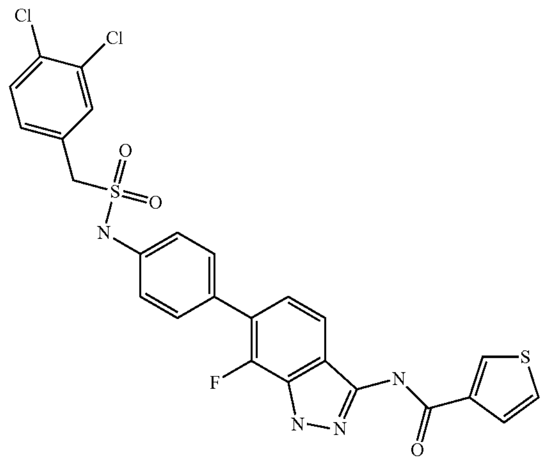 | Thiophene-3-carboxylic acid {6-[4-(3,4-dichlorophenyl-methanesulfonyl]-aminophenyl]-7-fluoro-1H-indazol-3-yl}-amide | | 122 mg 75% | IR spectrum: KBr 3425; 1659; 1528; 1339; 1157; 741 &593 cm$^{-1}$ NMR: 4.63 (s, 2H); 7.17 (dd, J = 7.0 and 8.5 Hz, 1H); from 7.27 to 7.33 (partially masked m, 1H); 7.31 (broad d, J = 8.5 Hz, 2H); 7.55 (d, J = 2.0 Hz, 1H); from 7.59 to 7.66 (m, 4H); 7.68 (dd, J = 3.0 and 5.0 Hz, 1H); 7.73 (broad d, J = 5.0 Hz, 1H); 8.48 (broad d, J = 2.5 Hz, 1H); 10.1 (s, 1H); 10.8 (s, 1H); 13.4 (broad s, 1H). |
| 36 | 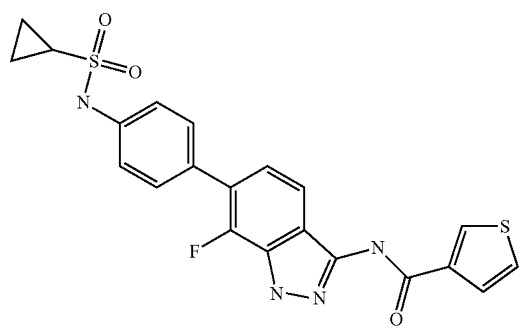 | Thiophene-3-carboxylic acid {6-[4-cyclopropanesulfonyl)-aminophenyl]-7-fluoro-1H-indazol-3-yl]-amide | | 101 mg 78% | IR spectrum: KBr 3351; 3175; 1642; 1528; 1332; 1299; 1268; 1137; 911 & 702 cm$^{-1}$ NMR: from 0.93 to 1.03 (m, 4H); 2.71 (m, 1H); 7.17 (dd, J = 7.0 and 8.5 Hz, 1H); 7.38 (broad d, J = 9.0 Hz, 2H); 7.59 to 7.64 (m, 3H); 7.68 (dd, J = 3.0 and 5.0 Hz, 1H); 7.72 (broad d, J = 5.0 Hz, 1H); 8.48 (broad d, J = 2.5 Hz, 1H); 9.91 (s, 1H); 10.8 (s, 1H); 13.4 (s, 1H). |

-continued

| Example Nº | Structure | Name | Sulfonyl chloride precursor | Amount Yield | Analyses |
|---|---|---|---|---|---|
| 37 | 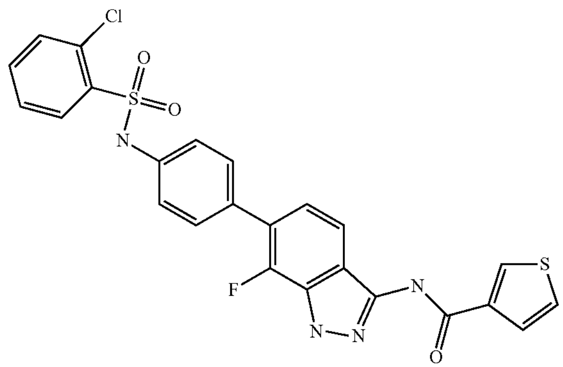 | Thiophene-3-carboxylic acid {6-[4-(2-chloro-benzenesulfonyl)-aminophenyl]-7-fluoro-1H-indazol-3-yl}-amide | | 107 mg 71% | IR spectrum: KBr 3351; 1660; 1527; 1339; 1162; 1044; 913; 748 &588 cm$^{-1}$ NMR: 7.09 (dd, J = 7.0 and 8.5 Hz, 1H); 7.23 (broad d, J = 9.0 Hz, 2H); 7.52 (broad d, J = 9.0 Hz, 2H); from 7.53 to 7.60 (m, 2H); from 7.62 to 7.68 (m, 3H); 7.71 (broad d, J = 5.0 Hz, 1H); 8.12 (broad d, J = 8.0 Hz, 1H); 8.46 (broad d, J = 2.5 Hz, 1H); 10.75 (s, 1H); 10.85 (s, 1H). |
| 38 | 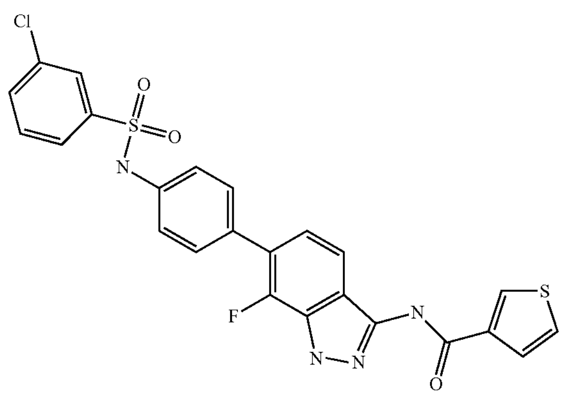 | Thiophene-3-carboxylic acid {6-[4-(3-chloro-benzenesulfonyl)-aminophenyl]-7-fluoro-1H-indazol-3-yl}-amide | | 137 mg 92% | IR spectrum: KBr 3424; 1652; 1528; 1340; 1183; 914; 679 &594 cm$^{-1}$ NMR: 7.11 (dd, J = 7.0 and 8.5 Hz, 1H); 7.24 (broad d, J = 9.0 Hz, 2H); 7.56 (broad d, J = 8.5 Hz, 2H); from 7.58 to 7.65 (m, 2H); 7.67 (dd, J = 3.0 and 5.0 Hz, 1H); 7.71 (broad d, J = 5.0 Hz, 1H); 7.74 (broad d, J = 8.0 Hz, 1H); 7.78 (broad d, J = 8.0 Hz, 1H); 7.83 (t, J = 1.5 Hz, 1H); 8.47 (broad d, J = 2.5 Hz, 1H); 10.6 (s, 1H); 10.8 (s, 1H); 13.4 (broad s, 1H); 13.35 (s, 1H). |

-continued

| Example N° | Structure | Name | Sulfonyl chloride precursor | Amount Yield | Analyses |
|---|---|---|---|---|---|
| 39 | (structure shown) | Thiophene-3-carboxylic acid {7-fluoro-6-[4-(1-methyl-1H-imidazole-4-sulfonylamino)-phenyl]-1H-indazol-3-yl}-amide | (structure shown) | 94 mg 67% | IR spectrum: KBr 3420; 1657; 1529; 1341; 1159; 1120; 913; 695; 624 &548 cm$^{-1}$ NMR: 3.67 (s, 3H); 7.11 (dd, J = 7.0 and 8.5 Hz, 1H); 7.28 (broad d, J = 9.0 Hz, 2H); 7.51 (broad d, J = 8.5 Hz, 2H); 7.60 (d, J = 8.5 Hz, 1H); 7.67 (dd, J = 3.0 and 5.0 Hz, 1H); 7.71 (broad d, J = 5.0 Hz, 1H); 7.76 (broad s, 1H); 7.89 (broad s, 1H); 8.47 (broad d, J = 2.5 Hz, 1H); 10.4 (s, 1H); 10.8 (s, 1H); 13.35 (broad s, 1H) |

EXAMPLES 40 TO 49

In Emrys Optimizer microwave tubes, solutions of each of examples 30 to 39 in 1.78 mL of methanol and 0.22 mL of a 37% hydrochloric acid solution are reacted with stirring in a microwave oven at 120° C. for 30 minutes. The solutions are concentrated under reduced pressure, taken up in 1 mL of dimethyl sulfoxide and purified by preparative LC/MS. The NMR analyses are conducted as follows: $^1$H NMR spectrum at 400 MHz on a BRUKER AVANCE DRX-400 spectrometer, with the chemical shifts (δ in ppm)—in dimethyl sulfoxide-d6 (DMSO-d6) as solvent, referenced at 2.50 ppm:

The products 40 to 42 and 44 to 49 are described in the following table:

| Example No. | Structure | Name | Precursor Quantity | Quantity Yield | Analyses |
|---|---|---|---|---|---|
| 40 | 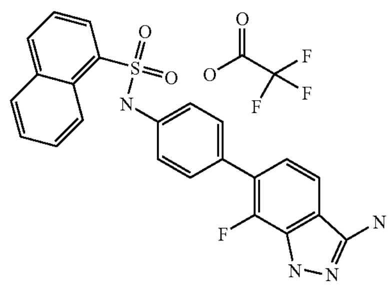 | Naphthalene-1-sulfonic acid [4-(3-amino-7-fluoro-1H-indazol-6-yl)-phenyl]-amide; compound with trifluoroacetic acid | Example 30 38 mg | 27 mg 71% | IR spectrum: KBr 3414; 1659; 1202; 1160; 1133; 912; 803; 770 &588 cm$^{-1}$ NMR: 6.87 (dd, J = 7.0 and 8.5 Hz, 1H); 7.14 (broad d, J = 9.0 Hz, 2H); 7.40 (broad d, J = 8.5 Hz, 2H); 7.50 (d, J = 8.5 Hz, 1H); from 7.63 to 7.71 (m, 2H); 7.75 (broad t, J = 8.0 Hz, 1H); 8.09 (broad d, J = 8.0 Hz, 1H); 8.24 (broad d, J = 8.0 Hz, 1H); 8.29 (broad d, J = 8.0 Hz, 1H); 8.75 (broad d, J = 8.0 Hz, 1H); 10.9 (s, 1H); from 11.7 to 12.2 (very spread-out m, 1H). |
| 41 | 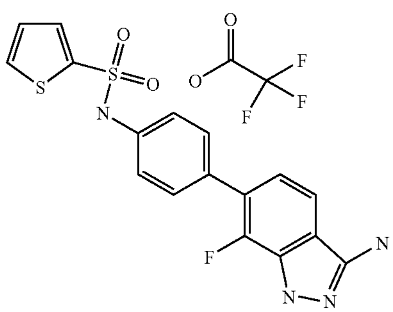 | Thiophene-2-sulfonic acid [4-(3-amino-7-fluoro-1H-indazol-6-yl)-phenyl]amide; compound with trifluoroacetic acid | Example 31 40 mg | 26 mg 74% | IR spectrum: KBr 3440; 3395; 3361; 1658; 1527; 1333; 1205; 1154; 1018; 800; 726 &589 cm$^{-1}$ NMR: 6.97 (dd, J = 7.0 and 8.5 Hz, 1H); 7.14 (dd, J = 4.0 and 5.0 Hz, 1H); 7.26 (broad d, J = 8.5 Hz, 2H); 7.52 (broad d, J = 8.5 Hz, 2H); 7.56 (d, J = 8.5 Hz, 1H); 7.62 (dd, J = 1.5 and 4.0 Hz, 1H); 7.92 (dd, J = 1.5 and 5.0 Hz, 1H); 10.6 (s, 1H); from 11.8 to 12.2 (very spread-out m, 1H). |
| 42 | 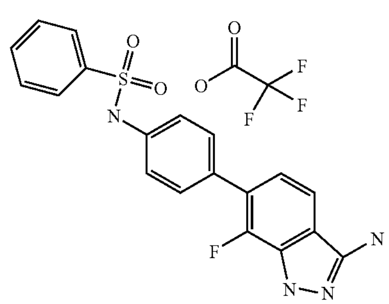 | N-[4-(3-Amino-7-fluoro-1H-indazol-6-yl)phenyl]benzene-sulfonamide; compound with trifluoroacetic acid | Example 32 30 mg | 13 mg 37% | IR spectrum: KBr 3392; 1659; 1202; 1159; 1090 & 590 cm$^{-1}$ NMR: 6.92 (dd, J = 7.0 and 8.5 Hz, 1H); 7.21 (broad d, J = 8.5 Hz, 2H); 7.47 (broad d, J = 8.5 Hz, 2H); 7.53 (d, J = 8.5 Hz, 1H); from 7.55 to 7.66 (m, 3H); 7.83 (broad d, J = 8.5 Hz, 2H); 10.5 (s, 1H); from 11.8 to 12.1 (spread-out m, 1H). |
| 44 | 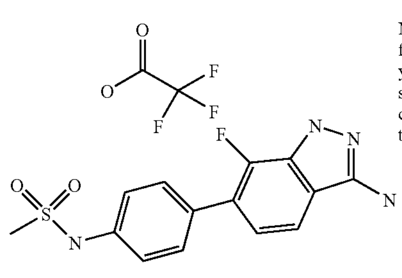 | N-[4-(3-Amino-7-fluoro-1H-indazol-6-yl)phenyl]methane-sulfonamide; compound with trifluoroacetic acid | Example 34 33 mg | 21 mg 69% | IR spectrum: KBr 3382; 1659; 1336; 1200; 1154; 981; 811; 727 &515 cm$^{-1}$ NMR: 3.05 (s, 3H); 7.02 (dd, J = 7.0 and 8.5 Hz, 1H); 7.32 (broad d, J = 8.5 Hz, 2H); 7.58 (broad d, J = 8.5 Hz, 3H); 9.90 (s, 1H); from 11.7 to 12.5 (very spread-out m, 1H). |

-continued

| Example No. | Structure | Name | Precursor Quantity | Quantity Yield | Analyses |
|---|---|---|---|---|---|
| 45 | 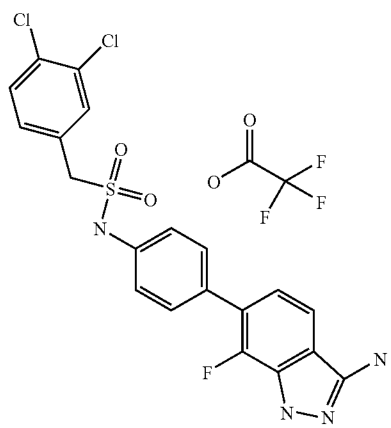 | N-[4-(3-Amino-7-fluoro-1H-indazol-6-yl)phenyl]-C-(3,4-dichlorophenyl)-methanesulfonamide; compound with trifluoroacetic acid | Example 35 42 mg | 29 mg 72% | IR spectrum: KBr 3358; 3192; 1678; 1611; 1471; 1339; 1205; 1140; 946; 806; 726 & 600 cm$^{-1}$ NMR 4.62 (s, 2H); 7.01 (dd, J = 7.0 and 8.5 Hz, 1H); 7.29 (broad d, J = 8.5 Hz, 2H); from 7.53 to 7.59 (m, 5H); 7.64 (d, J = 8.5 Hz, 1H); 10.05 (s, 1H); from 11.7 to 12.2 (spread-out m, 1H). |
| 46 | 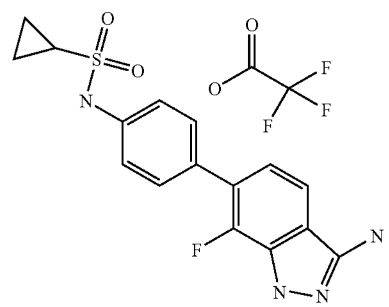 | Cyclopropanesulfonic acid [4-(3-amino-7-fluoro-1H-indazol-6-yl)phenyl]amide; compound with trifluoroacetic acid | Example 36 55 mg | 30 mg 93% | IR spectrum: KBr 3396; 1660; 1200; 1148; 913; 809 & 724 cm$^{-1}$ NMR: from 0.95 to 1.00 (m, 4H); 2.69 (m, 1H); 7.02 (dd, J = 7.0 and 8.5 Hz, 1H); 7.35 (broad d, J = 8.5 Hz, 2H); from 7.54 to 7.60 (m, 3H); 9.88 (s, 1H); from 11.8 to 12.3 (very spread-out m, 1H. |
| 47 | 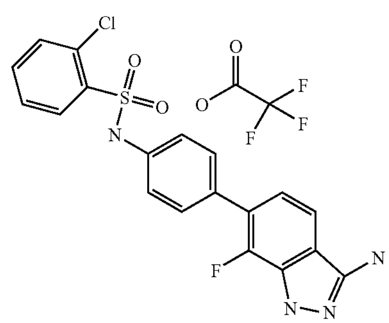 | N-[4-(3-Amino-7-fluoro-1H-indazol-6-yl)phenyl]-2-chloro-benzenesulfonamide; compound with trifluoroacetic acid | Example 37 42 mg | 25 mg 67% | IR spectrum: KBr 3414; 3254; 1657; 1532; 1344; 1190; 1163; 1044; 759&587 cm$^{-1}$ NMR: 6.92 (dd, J = 7.0 and 8.5 Hz, 1H); 7.20 (broad d, J = 8.5 Hz, 2H); 7.47 (broad d, J = 8.5 Hz, 2H); 7.52 (d, J = 8.5 Hz, 1H); 7.55 (m, 1H); from 7.62 to 7.68 (m, 2H); 8.11 (broad d, J = 8.0 Hz, 1H); 10.8 (s, 1H); from 11.7 to 12.2 (very spread-out m, 1H). |
| 48 | 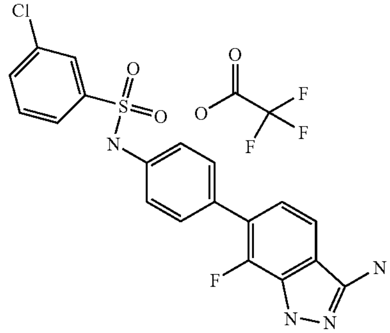 | N-[4-(3-Amino-7-fluoro-1H-indazol-6-yl)phenyl]-3-chloro-benzenesulfonamide; compound with trifluoroacetic acid | Example 38 | 15 mg | IR spectrum: KBr 3379; 1672; 1529; 1337; 1202; 1163; 912; 800; 679; 595 & 577 cm$^{-1}$ NMR: 6.94 (dd, J = 7.0 and 8.5 Hz, 7.22 (broad d, J = 8.5 Hz, 2H); 7.51 (broad d, J = 8.5 Hz, 2H); 7.54 (d, J = 8.5 Hz, 1H); 7.62 (t, J = 8.0 Hz, 1H); 7.72 (broad d, J = 8.0 Hz, 1H); 7.76 (broad d, J = 8.0 Hz, 1H); 7.81 (broad s, 1H); 10.6 (s, 1H); from 11.6 to 12.4 (very spread-out m, 1H). |

-continued

| Example No. | Structure | Name | Precursor Quantity | Quantity Yield | Analyses |
|---|---|---|---|---|---|
| 49 | (structure) | 1-Methyl-1H-imidazole-4-sulfonic acid [4-(3-amino-7-fluoro-1H-indazol-6-yl)phenyl]amide; compound with trifluoroacetic acid | Example 39 | 25 mg | IR spectrum: KBr 3397; 3132; 1659; 1337; 1200; 1157; 1118; 810; 725 &624 cm$^{-1}$ NMR: 3.66 (s, 3H); 6.98 (dd, J = 7.0 and 8.5 Hz, 1H); 7.26(broad d, J = 8.5 Hz, 2H); 7.47 (broad d, J = 8.5 Hz, 2H); 7.56 (d, J = 8.5 Hz, 1H); 7.76 (d, J =1 Hz, 1H); 7.88 (d, J = 1 Hz, 1H); 10.4 (s, 1H); from 11.55 to 12.7 (very spread-out m, 1H). |

Determination of the Activity of the Compounds—Experimental Protocols

1. KDR

The inhibitory effect of the compounds is determined in an assay of substrate phosphorylation by the KDR enzyme in vitro using a scintillation technique (96-well plate, NEN).

The cytoplasmic domain of the human KDR enzyme was cloned in the form of a GST fusion into the baculovirus expression vector pFastBac. The protein was expressed in SF21 cells and purified to approximately 60% homogeneity.

The KDR kinase activity is measured in 20 mM MOPS, 10 mM MgCl$_2$, 10 mM MnCl$_2$, 1 mM DTT, 2.5 mM EGTA, 10 mM β-glycerophosphate, pH=7.2, in the presence of 10 mM MgCl$_2$, 100 µM Na$_3$VO$_4$, 1 mM NaF. 10 µl of the compound are added to 70 µl of kinase buffer, containing 100 ng of KDR enzyme at 4° C. The reaction is triggered by adding 20 µl of solution containing 2 µg of substrate (SH2-SH3 fragment of PLCγ expressed in the form of a GST fusion protein), 2 µCi γ$^{33}$P[ATP] and 2 µM cold ATP. After 1 hour of incubation at 37° C., the reaction is stopped by adding 1 volume (100 µl) of 200 mM EDTA. The incubation buffer is withdrawn and the wells are washed three times with 300 µl of PBS. The radioactivity is measured in each well using a Top Count NXT radioactivity counter (Packard).

The background noise is determined by measuring the radioactivity in four different wells containing the radioactive ATP and the substrate alone.

A control for total activity is measured in four different wells containing all of the reagents (γ$^{33}$P-[ATP], KDR and PLCγ substrate), but in the absence of compound.

The inhibition of KDR activity with the compound of the invention is expressed in percentage inhibition of the control activity determined in the absence of compound.

The compound SU5614 (Calbiochem) (1 µM) is included in each plate as an inhibition control.

2. Tie2

The coding sequence of human Tie2, corresponding to the amino acids of the intracellular domain 776-1124, was generated by PCR, using the cDNA isolated from human placenta as a model. This sequence was introduced into a *baculovirus* expression vector pFastBacGT in the form of a GST fusion protein.

The inhibitory effect of the molecules is determined in an assay of PLC phosphorylation by Tie2 in the presence of GST-Tie2 purified to approximately 80% homogeneity. The substrate is composed of the SH2-SH3 fragments of PLC expressed in the form of a GST fusion protein.

The kinase activity of Tie2 is measured in a 20 mM MOPS buffer, pH 7.2, containing 10 mM MgCl$_2$, 10 mM MnCl$_2$, 1 mM DTT, 10 mM of glycerol-phosphate. In a 96-well Flash-Plate plate, kept on ice, a reaction mixture is deposited which is composed of 70 µl of kinase buffer containing 100 ng of GST-Tie2 enzyme per well. Subsequently 10 µl of the test molecule diluted to a concentration of 10% maximum in DMvSO are added. For a given concentration, each measurement is carried out in quadruplicate. The reaction is initiated by adding 20 µl of solution containing 2 µg of GST-PLC, 2 µM of cold ATP and 1 µCi of $^{33}$P[ATP]. After 1 hour of incubation at 37° C., the reaction is terminated by adding 1 volume (100 µl) of 200 mM EDTA. Following removal of the incubation buffer, the wells are washed three times with 300 µl of PBS. The radioactivity is measured on a Wallac Micro-Beta 1450.

The inhibition of Tie2 activity is calculated and expressed as a percentage inhibition relative to the control activity determined in the absence of compound.

3. Aurora1 and Aurora2

The inhibitory effect of compounds with respect to the kinases Aurora1 and Aurora2 is determined by an enzyme assay employing radioactivity detection.

The kinase activity of Aurora 1 and Aurora 2 is evaluated by the phosphorylation of the substrate Numa-histidine in the presence of radiolabeled ATP ([$^{33}$P]ATP), using 96-well Flashplate plates in which nickel chelate is fixed to the surface of the microplate. The amount of $^{33}$P phosphate incorporated in the NuMA substrate is proportional to the activity of the enzyme Aurora1 or Aurora2.

Proteins:

The proteins are produced in the protein production laboratory of the SanofiAventis group.

Aurora 1: recombinant complex Aurora-B/INCENP-C3, purified to approximately 50%, in which the N-terminal end of Aurora-B has been labeled with histidine.

Aurora 2: whole recombinant protein comprising an N-terminal histidine tail, expressed in *E. coli* and purified to more than 82%.

NuMA (nuclear protein that associates with the mitotic apparatus) fragment of 424 amino acids, expressed in *E. coli*, whose N-terminal end has been labeled with histidine and used as a substrate for the two Aurora enzymes.

Protocol:

The microplates used are 96-well Flash-Plate plates with nickel chelate (Perkin Elmer, model SMP107).

The products for evaluation are incubated in a reaction volume of 100 µL per well in the presence of 10 nM of Aurora 1 or Aurora 2, 500 nM of NuMA substrate in a buffer composed of 50 mM of Tris/HCl (pH 7.5), 50 mM NaCl, 5 mM MgCl$_2$ (Aurora-B) or 10 mM MgCl$_2$ (Aurora-A) and 1 mM of DTT, at 37° C.

In each well, 80 µL of the enzyme/substrate incubation buffer are distributed, followed by 10 µL of the product to be evaluated, in variable concentrations. The reaction is initiated by adding 1 µM of final ATP containing 0.2 µCi of [$^{33}$P]ATP (10 µL). After 30 minutes of incubation, the reaction is terminated by simply removing the reaction buffer and each well is washed twice with 300 µl of the Tris/HCl buffer. The radioactivity is then measured in each well by means of a scintillation apparatus, Packard, Top count model.

The control enzyme activity of Aurora is expressed by the number of counts per minute obtained within 30 minutes, after deduction of the background noise (reaction mixture not containing the enzyme). The evaluation of the various test products is expressed in percentage inhibition of the Aurora activity relative to the control.

4. CDK4/cyclin D1

Purification of the CDK4-HA/cyclin D1-(His)$_6$ complex by IMAC (Immobilized Metal Affinity Chromatography):

Two recombinant baculoviruses carrying the human sequences coding respectively for CDK4-HA (C-terminal fusion with the Hemagglutinin tag) and for cyclin D1-(His)$_6$ are used to co-infect Sf9 insect cells. Sixty hours after the beginning of co-infection, the cells are harvested by centrifugation and then frozen at −20° C. until their use. After thawing in buffer A (HEPES 200 mM pH 7.0, NaCl 50 mM, MgCl$_2$ 2 mM, imidazole 25 mM, TCEP 1 mM, glycerol 10% (w/v), NaF 1 mM, Na$_3$VO$_4$ 1 mM), stirring at 4° C. for 1 h, and centrifugation, the complex present in the lysis supernatant is purified by affinity chromatography on nickel (IMAC) and stored at −80° C.

CDK4/cyclinD1 Flashplate Assay in 96-Well Format.

An assay in 96-well "Flashplate" (scintillation plate) plates coated with streptavidin is used to evaluate the inhibition of the CDK4/cyclin D1 kinase complex by the products of the invention. To perform this test, the biotinylated peptide substrate, a fragment of the pRb protein, (biotinyl-RPPTL-SPIPHIPRSPYKFPSSPLR-amide), is dissolved at a concentration of 2 mM in kinase buffer (HEPES/NaOH 50 mM, NaCl 1 mM, MgCl$_2$ 5 mM, pH=7.5) to form a stock solution, which is stored at −20° C. in the form of 110 µl aliquots. On the day of the experiment, an aliquot of this solution is thawed and diluted in kinase buffer containing 1 mM of dithiothreitol, added at the time of use, so as to give a final peptide concentration of 2.571 µM. seventy µl of this solution are deposited in each well of the Flashplate plate, to give a final substrate concentration of 1.8 µM during the enzymatic reaction, which is performed in a final volume of 100 µl (cf. below). Intermediate dilutions of inhibitors (products of the invention) at various concentrations are prepared in DMSO from 10 mM stock solutions in separate tubes. In this way dilutions at 1000 µM, 333.3 µM, 111.1 µM, 37.03 µM, 12.35 µM, 4.11 µM and 1.37 µM are produced. One µl of each of these solutions (or 1 µl of DMSO for the controls) is subsequently transferred into the wells of the assay plate. To each well there is subsequently added 19 µl of a solution of a mixture of adenosine triphosphate (ATP) and ATPγ$^{33}$P in the kinase buffer at a concentration of 5.26 µM of total ATP and 78.9 µCi/ml of $^{33}$P. The enzymatic reaction is triggered by adding 10 µl per well of a solution of CDK4/cyclin D1 complex at 250 nM in the kinase buffer, containing 1 mM of dithiothreitol (or 10 µl of kinase buffer containing 1 mM of dithiothreitol for the reaction blanks). At the end of the various additions, the final volume in each well is 100 µl, the final substrate concentration is 1.8 µM, the final inhibitor concentrations are 10 µM, 3.33 µM, 1.11 µM, 0.37 µM, 0.123 µM, 0.041 µM and 0.014 µM (depending on the concentration of the intermediate dilution), the final ATP concentration is 1 µM, the final amount of $^{33}$P is 1.5 µCi/well, and the final concentration of CDK4/cyclin D1 complex is 25 nM.

After all of the reagents have been added, the assay plate is incubated at 30° C. with orbital stirring at 650 rpm. Following incubation, the plate is washed three times with 300 µl per well of PBS buffer (phosphate buffered saline, pH=7.4 with neither calcium nor magnesium, reference 10010-015, Gibco BRL). The incorporation of $^{33}$P into the substrate peptide is measured by scintillation counting using a Packard Topcount-.NXT instrument. The inhibitory activity of the products of the invention is evaluated by determining the concentration of inhibitor resulting in a 50% reduction in the enzymatic activity (IC50).

TABLE 1

Results:

| Structure | Example | KDR | TIE2 | Aurora2 | CDK4 |
|---|---|---|---|---|---|
| (CF$_3$, F-substituted diphenylurea linked to 1H-indazol-3-amine) | 1 | 33 | 1785 | 113 | nd |

TABLE 1-continued
Results:
| Structure | Example | IC 50 (nM) | | | |
|---|---|---|---|---|---|
| | | KDR | TIE2 | Aurora2 | CDK4 |
| 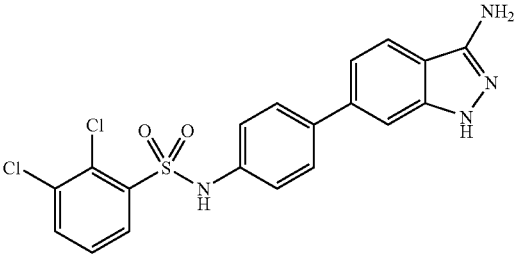 | 2 | 10000 | 15 | 200 | 132 |
| 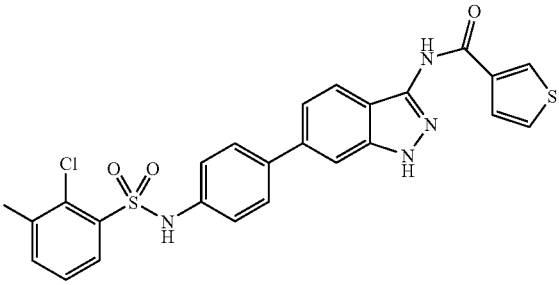 | 3 | 864 | 4 | 133 | 145 |
| 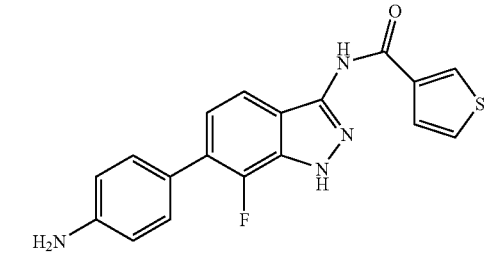 | 4 | 164 | 799 | 465 | nd |
| 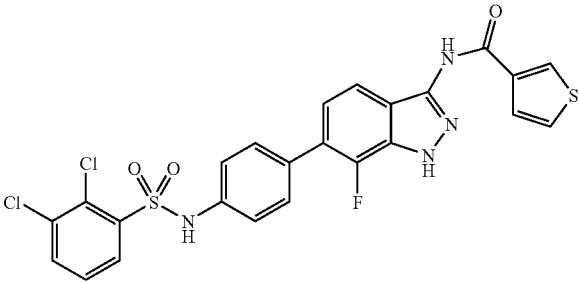 | 5 | 1873 | 2 | 37 | 55 |
| 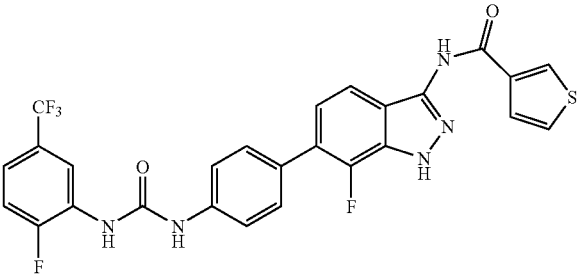 | 6 | 8 | 9 | 36 | nd |

TABLE 1-continued
| Structure | Example | KDR | TIE2 | Aurora2 | CDK4 |
|---|---|---|---|---|---|
| 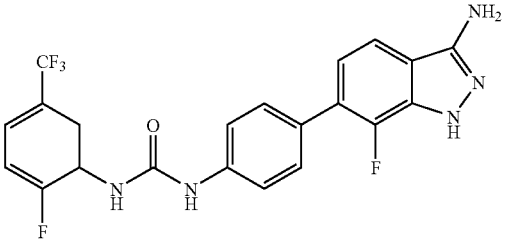 | 7 | 122 | 51 | 172 | nd |
| 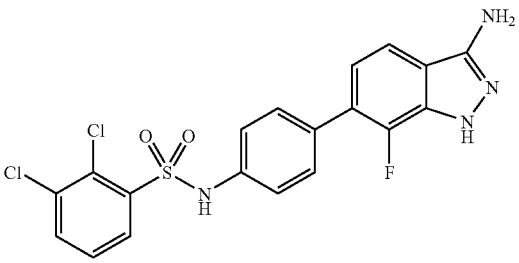 | 8 | 6585 | 10 | 87 | 117 |
| 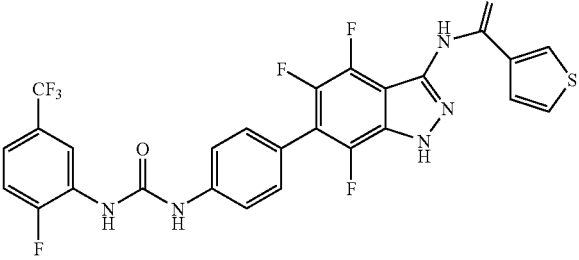 | 9 | 693 | 46 | 1751 | nd |
| 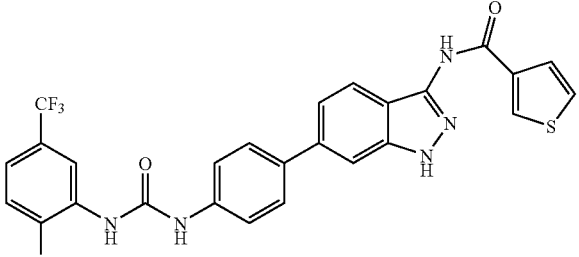 | 10 | 166 | 18 | 171 | nd |
| 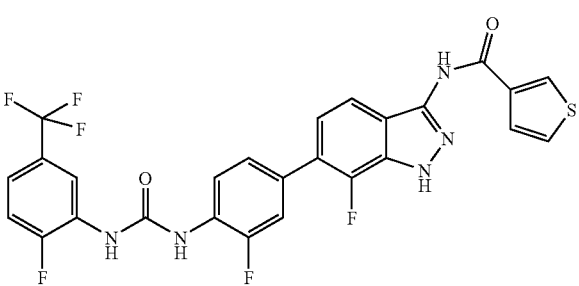 | 11 | 37 | 11 | 185 | nd |
IC 50 (nM)

TABLE 1-continued

Results:

| Structure | Example | IC 50 (nM) | | | |
|---|---|---|---|---|---|
| | | KDR | TIE2 | Aurora2 | CDK4 |
| 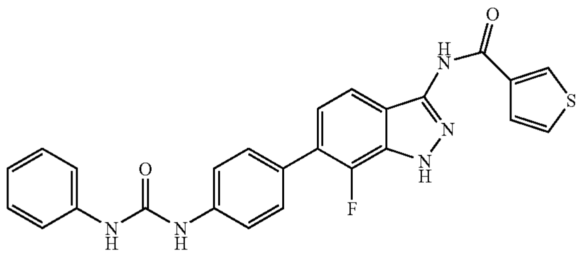 | 12 | 2771 | 36 | 14 | nd |
| 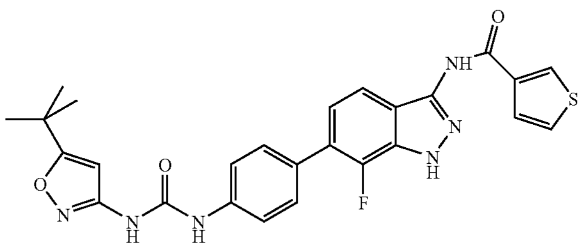 | 13 | 29 | 31 | 65 | nd |
| 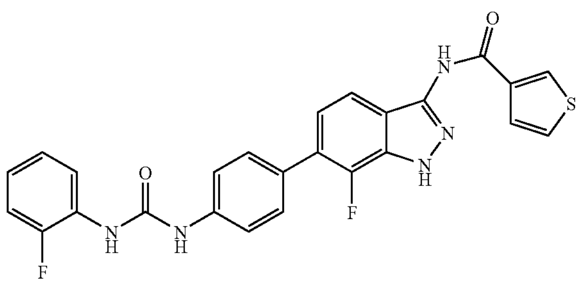 | 14 | 4216 | 50 | 23 | nd |
| 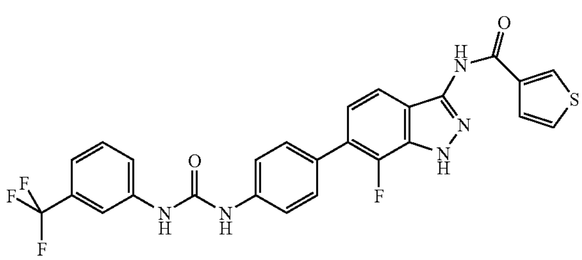 | 15 | 40 | 20 | 28 | nd |
| 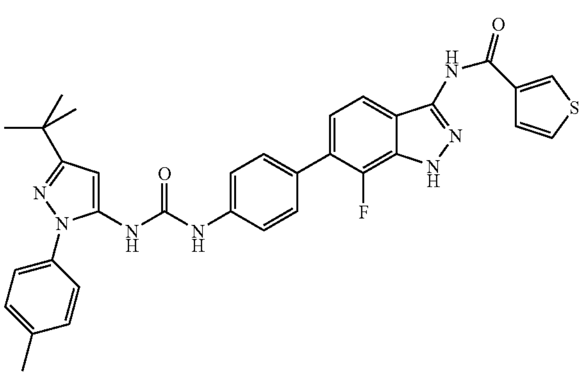 | 16 | 19 | 3 | 142 | nd |

TABLE 1-continued

Results:

| Structure | Example | IC 50 (nM) | | | |
|---|---|---|---|---|---|
| | | KDR | TIE2 | Aurora2 | CDK4 |
| (structure) | 17 | 29 | 8 | 60 | nd |
| (structure) | 18 | 77 | 26 | 346 | nd |
| (structure) | 19 | 329 | 231 | 92 | nd |
| (structure) | 20 | 10000 | 502 | 63 | nd |
| (structure) | 21 | 85 | 174 | 68 | nd |
| (structure) | 22 | 1944 | 5850 | 143 | nd |

TABLE 1-continued

| Structure | Example | IC 50 (nM) | | | |
| --- | --- | --- | --- | --- | --- |
| | | KDR | TIE2 | Aurora2 | CDK4 |
| 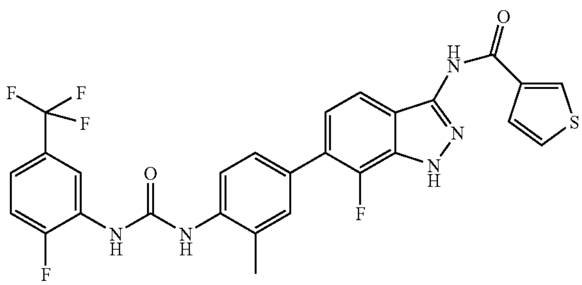 | 23 | 15 | 16 | 296 | nd |
| 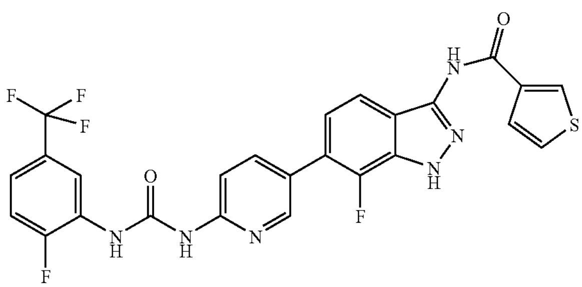 | 24 | 10000 | 229 | 10000 | nd |
| 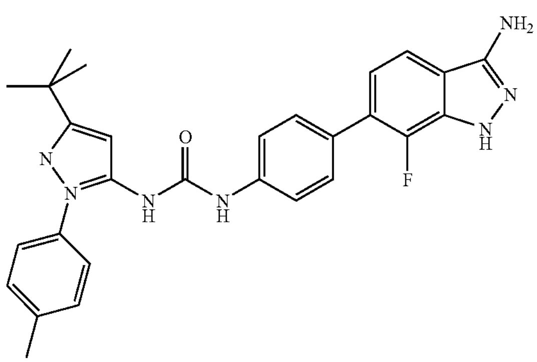 | 25 | 11 | 17 | 94 | nd |
| 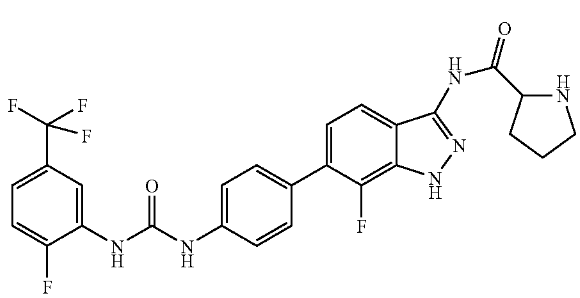 | 26 | 1055 | 626 | 3378 | nd |

TABLE 1-continued

| Structure | Example | IC 50 (nM) | | | |
| --- | --- | --- | --- | --- | --- |
| | | KDR | TIE2 | Aurora2 | CDK4 |
| (structure) | 27 | 79 | 143 | 335 | nd |
| (structure) | 28 | 164 | 176 | 520 | nd |
| See compound 4 | 29 | 164 | 799 | 465 | nd |
| (structure) | 30 | nd | nd | nd | 490 |
| (structure) | 31 | nd | nd | nd | 730 |

TABLE 1-continued

| Structure | Example | IC 50 (nM) | | | |
| --- | --- | --- | --- | --- | --- |
| | | KDR | TIE2 | Aurora2 | CDK4 |
| (structure) | 32 | nd | nd | nd | 747 |
| (structure) | 33 | nd | nd | nd | 1214 |
| (structure) | 34 | nd | nd | nd | 2089 |
| (structure) | 35 | nd | nd | nd | nd |

TABLE 1-continued

Results:

| Structure | Example | IC 50 (nM) | | | |
|---|---|---|---|---|---|
| | | KDR | TIE2 | Aurora2 | CDK4 |
| (structure) | 36 | nd | nd | nd | 3604 |
| (structure) | 37 | nd | nd | nd | 51 |
| (structure) | 38 | nd | nd | nd | 419 |
| (structure) | 39 | nd | nd | nd | 3647 |

TABLE 1-continued

| Structure | Example | IC 50 (nM) | | | |
|---|---|---|---|---|---|
| | | KDR | TIE2 | Aurora2 | CDK4 |
| [naphthalene-SO2-NH-phenyl-(7-fluoro-3-amino-1H-indazol-6-yl), TFA salt] | 40 | nd | nd | nd | nd |
| [thiophene-2-SO2-NH-phenyl-(7-fluoro-3-amino-1H-indazol-6-yl), TFA salt] | 41 | nd | nd | nd | nd |
| [phenyl-SO2-NH-phenyl-(7-fluoro-3-amino-1H-indazol-6-yl), CF3COOH] | 42 | nd | nd | nd | nd |
| [4-aminophenyl-SO2-NH-phenyl-(7-fluoro-3-amino-1H-indazol-6-yl), CF3COOH] | 43 | nd | nd | nd | nd |

TABLE 1-continued
Results:
| Structure | Example | IC 50 (nM) | | | |
|---|---|---|---|---|---|
| | | KDR | TIE2 | Aurora2 | CDK4 |
| 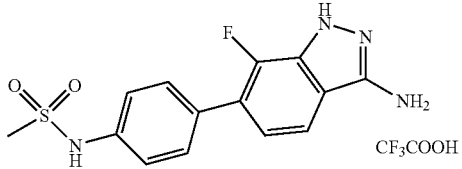 | 44 | nd | nd | nd | nd |
| 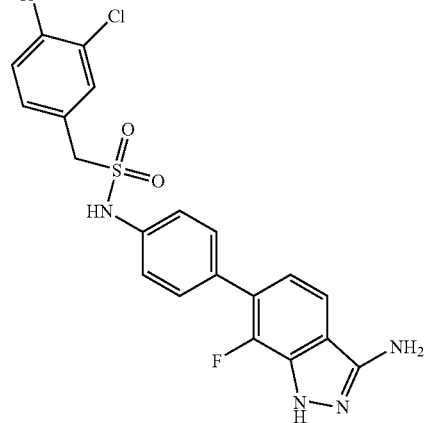 | 45 | nd | nd | nd | nd |
| 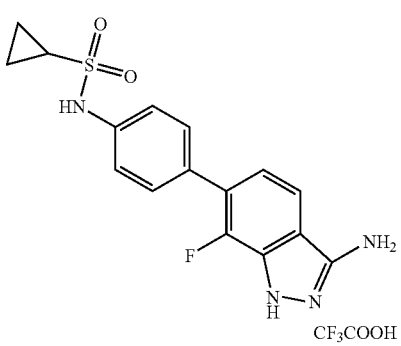 | 46 | nd | nd | nd | nd |
| 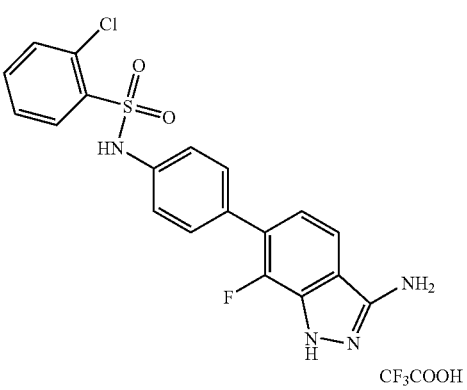 | 47 | nd | nd | nd | nd |

TABLE 1-continued

| | | IC 50 (nM) | | | |
|---|---|---|---|---|---|
| Structure | Example | KDR | TIE2 | Aurora2 | CDK4 |
| 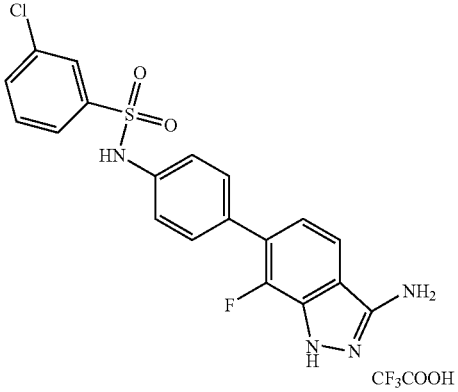 | 48 | nd | nd | nd | nd |
| 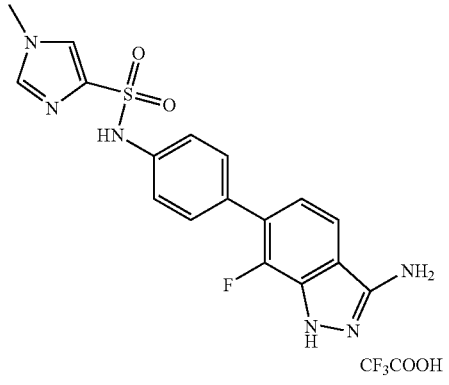 | 49 | nd | nd | nd | nd | is: intermediate in synthesis
nd: non determined

What is claimed is:

1. A compound according to formula (I):

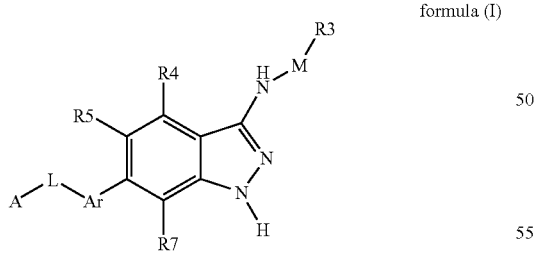

formula (I)

wherein:

A is selected from the group consisting of: H, aryl, heteroaryl, substituted aryl, and substituted heteroaryl;

Ar is selected from the group consisting of: aryl, heteroaryl, substituted aryl, and substituted heteroaryl;

L is selected from the group consisting of: NH—SO$_2$, SO$_2$NH, and NH—CO—NH;

M is selected from the group consisting of: a bond, CO, NH, CO—NH, CS—NH, NH—CO, NH—SO, NH—SO$_2$, CO—NH—SO$_2$, NH—CH$_2$, CH$_2$—CO—NH, NH—CO—CH$_2$, NH—CH$_2$—CO, and CO—CH$_2$—NH;

R3 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, and substituted alkynyl;

R4 and R5 are independently selected from the group consisting of: H, halogen, R2, CN, O(R2), OC(O)(R2), OC(O)N(R2)(R1), OS(O$_2$)(R2), N(R2)(R1), N=C(R2)(R1), N(R2)C(O)(R1), N(R2)C(O)O(R1), N(R6)C(O)N(R2)(R1), N(R6)C(S)N(R2)(R1), N(R2)S(O$_2$)(R1), C(O)(R2), C(O)O(R2), C(O)N(R2)(R1), C(=N(R1))(R2), C(=N(OR1))(R2), S(R2), S(O)(R2), S(O$_2$)(R2), S(O$_2$)O(R2), and S(O$_2$)N(R2)(R1); wherein each R2, R1, R6 is independently selected from the group consisting of H, alkyl, alkylene, alkynyl, aryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, and substituted alkynyl; wherein, when R2 and R1 are simultaneously present on one of R4 and R5, they may be linked to one another to form a ring;

R7 is fluoro;

or a pharmaceutically acceptable salt thereof.

2. The compound according to claim 1, wherein Ar-L-A is:

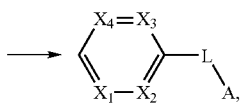

in which each X1, X2, X3 and X4 is independently selected from N and C—R11, wherein R11 is selected from the group consisting of: H, halogen, R2, CN, O(R2), OC(O)(R2), OC(O)N(R2)(R1), OS(O₂)(R2), N(R2)(R1), N=C(R2)(R1), N(R2)C(O)(R1), N(R2)C(O)O(R1), N(R6)C(O)N(R2)(R1), N(R6)C(S)N(R2)(R1), N(R2)S(O₂)(R1), C(O)(R2), C(O)O (R2), C(O)N(R2)(R1), C(=N(R1))(R2), C(=N(OR1))(R2), S(R2), S(O)(R2), S(O₂)(R2), S(O₂)O(R2), and S(O₂)N(R2) (R1); wherein each R2, R1, and R6 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, and substituted alkynyl; wherein, when R2 and R1 are simultaneously present on R11, they may be linked to one another to form a ring.

3. The compound according to claim 2, wherein R11 is selected from the group consisting of H, F, Cl, methyl, NH₂, OCF₃, and CONH₂.

4. The compound according to claim 1, wherein R4 and R5 are independently selected from H, F, Cl, Br and methyl.

5. The compound according to claim 1, wherein R4 is H.

6. The compound according to claim 1, wherein R5 is H.

7. The compound according to claim 1, wherein L-A is selected from NH—CO—NH-A and NH—SO₂-A.

8. The compound according to claim 7, wherein A is selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl, and benzothiazolyl; which are all optionally substituted.

9. The compound according to claim 8, wherein A is selected from phenyl, isoxazolyl, substituted phenyl, and substituted isoxazolyl.

10. The compound according to claim 7, wherein A is substituted by a first substituent selected from the group consisting of alkyl, halogenated alkyl, alkylene, alkynyl, aryl, O-alkyl, O-aryl, O-heteroaryl, S-alkyl, S-aryl, S-heteroaryl, each being optionally substituted by a substituent selected from (C1-C3)alkyl, halogen, O—(C1-C3)alkyl.

11. The compound according to claim 7, wherein A is substituted by a second substituent selected from the group consisting of F, Cl, Br, I, OH, SH, SO₃M, COOM, CN, NO₂, CON(R8)(R9), N(R8)(R9)CO(R8), (C1-C3)alkyl-OH, (C1-C3)alkyl-N(R8)(R9), (C1-C3)alkyl-(R10), (C1-C3)alkyl-COOH, and N(R8)(R9); in which R8 and R9 are independently selected from H, (C1-C3)alkyl, (C1-C3)alkylOH, (C1-C3)alkylNH₂, (C1-C3)alkylCOOM, and(C1-C3) alkylSO₃M; in which, when R8 and R9 are simultaneously other than H, they may be linked to form a ring; M is H or an alkali metal cation selected from Li, Na and K; and in which R10 is H or an optionally substituted nonaromatic heterocycle comprising 2 to 7 carbon atoms, and 1 to 3 heteroatoms selected from N, O and S.

12. The compound according to claim 7, wherein A is phenyl or isoxazolyl which is substituted by halogen, (C1-C4)alkyl, halogenated (C1-C3)alkyl, O—(C1-C4)alkyl, S—(C1-C4)alkyl, halogenated O—(C1-C4)alkyl, or halogenated S—(C1-C4)alkyl.

13. The compound according to claim 1, wherein M is selected from the group consisting of a bond, CO, CO—NH, and SO₂.

14. The compound according to claim 1, wherein R3 is selected from the group consisting of aryl, heteroaryl, substituted aryl, and substituted heteroaryl.

15. The compound according to claim 14, wherein R3 is substituted heteroaryl.

16. The compound according to claim 15, wherein the heteroaryl is selected from thienyl, pyrrolyl, furyl, indolyl, oxazolyl, isoxazolyl, thiazolyl, isothiazolyl, imidazolyl, indazolyl, pyridyl, pyrimidyl, pyrazolyl, and pyridazinyl.

17. The compound according to claim 1, wherein R4 and R5 are H.

18. The compound according to claim 1, selected from the group consisting of:

1-[4-(3-amino-7-fluoro-1H-indazol-6-yl)phenyl]-3-(2-fluoro-5-trifluoromethyl-phenyl)urea;

1-(2-fluoro-5-trifluoromethylphenyl)-3-{4-[7-fluoro-3-(thiophen-3-yl-carbonylamino)-1H-indazol-6-yl] phenyl}urea;

N-{6-[4-(2,3-dichlorobenzenesulfonylamino)phenyl]-7-fluoro-1H-indazol-3-yl}-(thiophen-3-yl-carboxamide);

N-[4-(3-amino-7-fluoro-1H-indazol-6-yl)phenyl]-2,3-dichlorobenzenesulfonamide; and 1-(2-fluoro-5-trifluoromethylphenyl)-3-{4-[4,5,7-trifluoro-3-(thiophen-3-yl-carbonylamino)-1H-indazol-6-yl]phenyl}urea;

or a pharmaceutically acceptable salt thereof.

19. The compound according to claim 1, selected from the group consisting of:

1-[4-(3-amino-7--fluoro-1H-indazol-6-yl)-phenyl]-2,3-dichlorobenzenesulfonamide hydrochloride;

1-(4-(4,5,7-Trifluoro-3-[(thiophen-3-yl)carbonylamino]-1H-indazol-6-yl}phenyl)-3-(2-fluoro-5-trifluoromethylphenyl)urea;

1-(4-{7-fluoro-3-[(thiophen-3-yl)carbonylamino]-1H-indazol-6-yl}-2-fluorophenyl)-3-(2-fluoro-5-trifluoromethylphenyl)urea;

1-(4-{7-fluoro-3-[(thiophen-3-yl)carbonylamino]-1H-indazol-6-yl}phenyl)-3-phenylurea;

1-(4-{7-fluoro-3-[(thiophen-3-yl)carbonylamino]-1H-indazol-6-yl}phenyl)-3-(5-tert-butylisoxazol-3-yl)urea;

1-(4-{7-fluoro-3-[(thiophen-3-yl)carbonylamino]-1H-indazol-6-yl}phenyl)-3-(2-fluorophenyl)urea;

1-(4-{7-fluoro-3-[(thiophen-3-yl)carbonylamino]-1H-indazol-6-yl}phenyl)-3-(5-trifluoromethylphenyl)urea;

1-(4-{7-fluoro-3-[(thiophen-3-yl)carbonylamino]-1H-indazol-6-yl}phenyl)-3-(5-tert-butyl-2-p-tolyl-2H-pyrazol-3-yl)urea;

1-(4-{7-fluoro-3-[(furan-2-yl)carbonylamino]-1H-indazol-6-yl}phenyl)-3-(2-fluoro-5-trifluoromethylphenyl) urea;

1-(4-{7-fluoro-3-[phenylcarbonylamino]-1H-indazol-6-yl}phenyl)-3-(2-fluoro-5-trifluoromethylphenyl)urea;

1-[4-(3-amino-7-fluoro-1H-indazol-6-yl)phenyl]-3-(3-trifluoromethylphenyl)urea;

1-[4-(3-amino-7-fluoro-1H-indazol-6-yl)phenyl]-3-phenylurea;

1-[4-(3-amino-7-fluoro-1H-indazol-6-yl)phenyl]-3-(5-tert-butylisoxazol-3-yl)urea;

1-[4-(3-amino-7-fluoro-1H-indazol-6-yl)phenyl]-3-(2-fluorophenyl)urea;

1-(4-{7-fluoro-3-[(thiophen-3-yl)carbonylamino]-1H-indazol-6-yl}-2-methylphenyl)-3-(2-fluoro-5-trifluoromethylphenyl)urea;

1-(5-{7-fluoro-3-[(thiophen-3-yl)carbonylamino]-1H-indazol-6-yl}pyridin-2-yl)-3-(2-fluoro-5-trifluoromethylphenyl)urea;

1-[4-(3-amino-7-fluoro-1H-indazol-6-yl)phenyl]-3-(5-tert-butyl-2-p-tolyl-2H-pyrazol-3-yl)urea;

1-(4-{7-fluoro-3-[(L-pyrrolidin-2-yl)carbonylamino]-1H-indazol-6-yl}phenyl)-3-(2-fluoro-5-trifluoromethylphenyl)urea;

1-(4-{7-fluoro-3-acetylamino-1H-indazol-6-yl}phenyl)-3-(2-fluoro-5-trifluoromethylphenyl)urea; and 1-(4-{7-fluoro-3-formylamino-1H-indazol-6-yl}phenyl)-3-(2-fluoro-5-trifluoromethylphenyl)urea;

or a pharmaceutically acceptable salt thereof.

20. The compound according to claim 1, selected from the group consisting of:

Thiophene-3-carboxylic acid {7-fluoro-6-[4-(naphthalene-1-sulfonylamino)-phenyl]-1H-indazol-3-yl}-amide;

Thiophene-3-carboxylic acid {7-fluoro-6-[4-(thiophene-2-sulfonylamino)-phenyl]-1H-indazol-3-yl}-amide;

Thiophene-3-carboxylic acid [6-(4-benzenesulfonylaminophenyl)-7-fluoro-1H-indazol-3-yl]amide;

Thiophene-3-carboxylic acid {6-[4-(4-acetylaminobenzenesulfonylamino)phenyl]-7-fluoro-1H-indazol-3-yl}amide;

Thiophene-3-carboxylic acid {6-[4-(2-chloro-benzenesulfonylamino)phenyl]-7-fluoro-1H-indazol-3-yl}-amide;

Thiophene-3-carboxylic acid {6-[4-(3-chloro-benzenesulfonylamino)phenyl]-7-fluoro-1H-indazol-3-yl}-amide; and Thiophene-3-carboxylic acid {7-fluoro-6-[4-(1-methyl-1H-imidazole-4-sulfonylamino)-phenyl]-1H-indazol-3-yl}-amide;

or a pharmaceutically acceptable salt thereof.

21. The compound according to claim 1, selected from the group consisting of:

Naphthalene-1-sulfonic acid [4-(3-amino-7-fluoro-1H-indazol-6-yl)-phenyl]-amide;

Thiophene-2-sulfonic acid [4-(3-amino-7-fluoro-1H-indazol-6-yl)-phenyl]amide;

N-[4-(3-Amino-7-fluoro-1H-indazol-6-yl)phenyl]benzenesulfonamide;

N-[4-(3-Amino-7-fluoro-1H-indazol-6-yl)phenyl]-2-chloro-benzenesulfonamide;

N-[4-(3-Amino-7-fluoro-1H-indazol-6-yl)phenyl]-3-chloro-benzenesulfonamide; and

1-Methyl-1H-imidazole-4-sulfonic acid [4-(3-amino-7-fluoro-1H-indazol-6-yl)phenyl]amide;

or a pharmaceutically acceptable salt thereof.

22. The compound according to claim 1, which is:
1) nonchiral, or
2) racemic, or
3) stereoisomerically enriched, or
4) enantiomerically enriched form;

and in that it is optionally converted to salt form.

23. A pharmaceutical composition comprising a compound according to claim 1 in combination with a pharmaceutically acceptable excipient.

* * * * *